(12) United States Patent
Lee

(10) Patent No.: US 7,857,622 B2
(45) Date of Patent: Dec. 28, 2010

(54) DENTAL ARTICULATOR

(75) Inventor: Tomas E. Lee, Grand Terrace, CA (US)

(73) Assignee: Panadent Corporation, Colton, CA (US)

( * ) Notice: Subject to any disclaimer, the term of this patent is extended or adjusted under 35 U.S.C. 154(b) by 864 days.

(21) Appl. No.: 11/542,349

(22) Filed: Oct. 2, 2006

(65) Prior Publication Data

US 2007/0134619 A1   Jun. 14, 2007

Related U.S. Application Data

(60) Provisional application No. 60/749,379, filed on Dec. 12, 2005.

(51) Int. Cl.
*A61C 11/00* (2006.01)
(52) U.S. Cl. ........................................................ 433/57
(58) Field of Classification Search ............. 433/54–67; 434/264
See application file for complete search history.

(56) References Cited

U.S. PATENT DOCUMENTS

| | | | |
|---|---|---|---|
| 3,593,424 A | 7/1971 | Lee | |
| 3,694,919 A | 10/1972 | Lee et al. | |
| 3,896,550 A | 7/1975 | Lee | |
| 4,034,475 A | 7/1977 | Lee | |
| 4,189,837 A * | 2/1980 | Stele ............................ 433/57 |
| 4,209,909 A | 7/1980 | Lee | |
| 4,352,662 A | 10/1982 | Lee | |
| 4,543,062 A | 9/1985 | Lee | |
| 4,556,387 A | 12/1985 | Lee | |
| 4,600,385 A | 7/1986 | Lee | |
| 4,693,683 A | 9/1987 | Lee | |
| 4,721,463 A | 1/1988 | Lee | |
| 5,738,515 A * | 4/1998 | Leever ......................... 433/55 |
| 5,934,901 A * | 8/1999 | Huffman ...................... 433/54 |
| 6,109,917 A | 8/2000 | Lee et al. | |
| 6,582,931 B1 | 6/2003 | Kois et al. | |
| 7,083,410 B2 * | 8/2006 | Callne .......................... 433/58 |
| 2004/0197729 A1 * | 10/2004 | Honstein et al. .............. 433/34 |

OTHER PUBLICATIONS

Cbite, Inc, "All Stone II" products, printed from the internet on Nov. 5, 2005.
Kois Dento—Facial Analyzer System article, published prior to Oct. 2, 2006.
Panadent, "Combining Esthetics and Function", published prior to Oct. 2, 2006.
Panadent, Articulator System, published prior to Oct. 2, 2006.

(Continued)

*Primary Examiner*—Cris L Rodriguez
*Assistant Examiner*—Matthew M Nelson
(74) *Attorney, Agent, or Firm*—Knobbe Martens Olson & Bear LLP

(57) ABSTRACT

A dental articulator includes an articulator frame. The articulator frame has an upper member adapted to hold an upper mounting plate. The upper mounting plate holds an upper dental cast. An elongate lower member of the frame holds a lower mounting plate. The lower mounting plate holds a lower dental cast. The upper member is pivotally connected to the lower member so as to define an anatomically accurate hinge axis to simulate human jaw movement. The dental articulator can be used to form dental prostheses.

31 Claims, 22 Drawing Sheets

OTHER PUBLICATIONS

Panadent, "Bio-Esthetic Level Gauge" brochure, 1997.

Denistry Today, Aesthetics—Standardized Head Position and Reference Planes for Dento-Facial Aesthetics, by Robert L. Lee, MS, DDS, vol. 19 No. 2, Feb. 2000.

"Introducing the Acculator"—The Affordable Way to Assess Occlusion, published prior to Oct. 2, 2006.

Canyon State Dental Supply—Articulators (Plastic), last modified Sep. 30, 2006.

Dentsply Ceramco, "Vertex Articulators", printed from internet on Oct. 23, 2006.

* cited by examiner

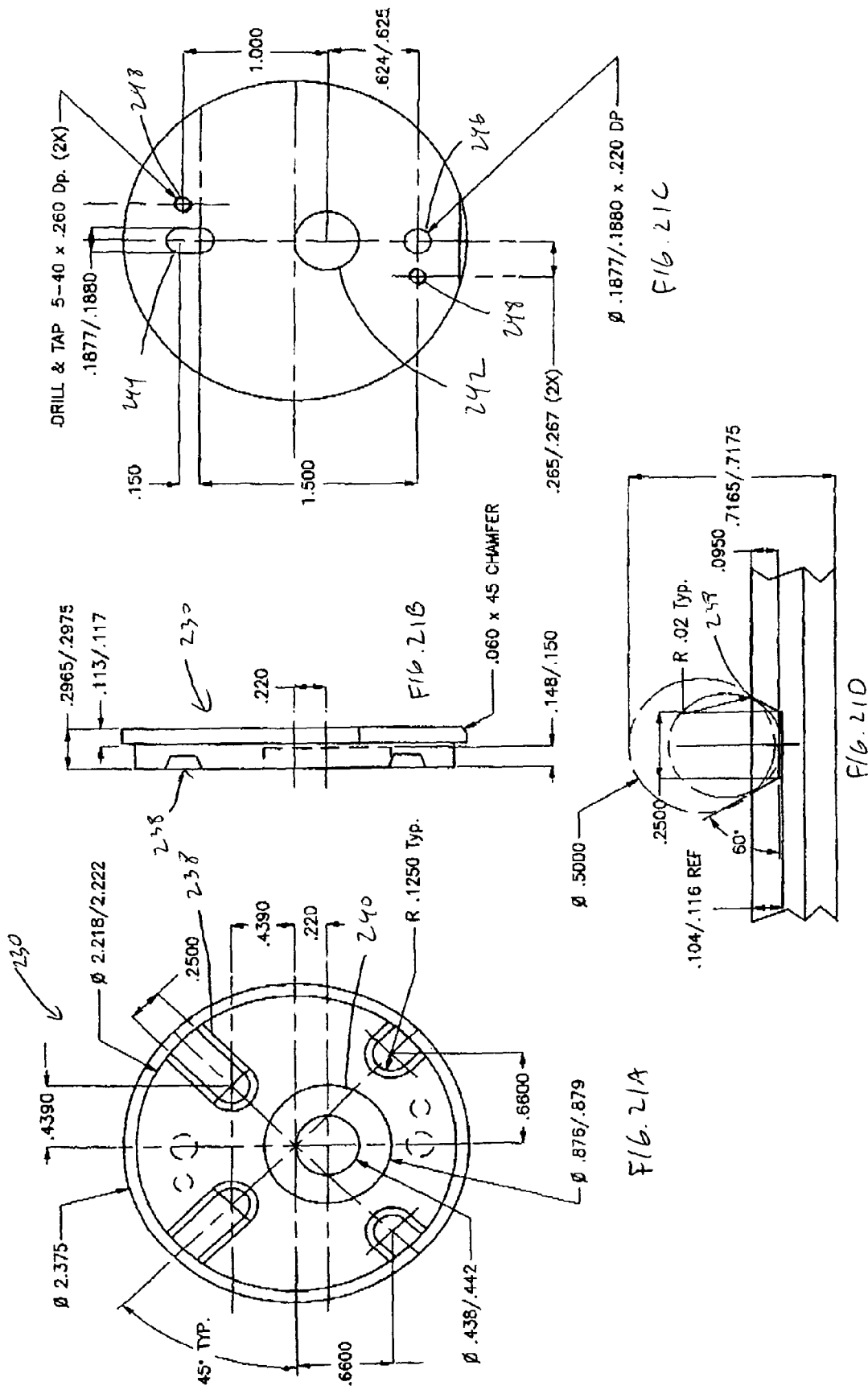

DENTAL ARTICULATOR

CROSS-REFERENCE TO RELATED APPLICATIONS

This application claims the benefit of U.S. Provisional Application No. 60/749,379, filed Dec. 12, 2005, the entirety of which is hereby incorporated by reference.

BACKGROUND OF THE INVENTION

1. Field of the Invention

The present invention relates to dental apparatuses, and more particularly to dental articulators.

2. Description of the Related Art

Dental articulators are used in the field of dentistry, including the fields of prosthodontics, restorative dentistry, implantology, orthodontics, and oral surgery. Prosthodontics are used as a replacement or substitute for natural teeth. The field of fixed prosthodontics generally relates to nonremovable replacements or substitutes for natural teeth, such as bridges and caps. The field of removable prosthodontics includes removable dentures. Dental articulators are used in both fields in making these dental prostheses. Full-size dental articulators often have the ability to simulate closely the actual centric, lateral, and protrusive jaw movements of the patient in order that the prosthodontist may produce a comfortable and effective dental prosthesis. Unfortunately, these dental articulators are relatively expensive and are somewhat bulky to be conveniently held and manipulated in a user's hand. These dental articulators are typically stationary systems that remain on a support surface during use.

Handheld dental articulators are also used by prosthodontists. Unfortunately, handheld dental articulators have axes of rotation that do not adequately simulate movement of a patient's jaw. Thus, prostheses made with these articulators often do not properly fit when implanted or placed in a patient.

SUMMARY OF THE INVENTION

Dental articulators can be used to simulate various positions and movements of a person's jaw. Articulators can aid in occlusal/occlusion diagnosis, developing a treatment plan, constructing prostheses, acquiring base line records, communicating with laboratories, didactics, prosthesis fabrication, and the like. A handheld dental articulator can be used to simulate the position and movement of a person's jaw. Advantageously, the handheld dental articulator can be an average value articulator that can simulate an average person's jaw movement. The handheld dental articulator can be used in conjunction with one or more of the following: aesthetic instruments, average value articulators, semi-adjustable articulators, fully-adjustable articulators, full-size articulators, handheld articulators, and other types of articulators. Various combinations of these instruments can be used to achieve the desired aesthetics and/or functionality as desired.

In some embodiments, a dental articulator includes an articulator frame. The articulator frame has an upper member adapted to hold an upper mounting plate. The upper mounting plate is configured to hold an upper dental cast. An elongate lower member of the articulator frame is configured to hold a lower mounting plate. The lower mounting plate is configured to hold a lower dental cast. The upper member is actuatable relative to the lower member so as to substantially simulate movement of the patient's jaw from which the upper and lower dental casts were made and related. In some variations, the dental articulator is a portable articulator. In some variations, the dental articulator is disposable. In some variations, the dental articulator is reusable and can be used any number of times, as desired.

In some embodiments, a dental articulator comprises an articulator frame. The articulator frame includes an upper member adapted to hold an upper mounting plate. The upper mounting plate is configured to hold an upper dental cast. An elongate lower member is adapted to hold a lower mounting plate. The lower mounting plate is configured to hold a lower dental cast. The upper member is pivotally connected to the lower member so as to define an axis of rotation that substantially simulates movement of a patient's jaw from which the upper and lower dental casts were made and related.

Mounting plates can be compatible with various types of articulators. For example, the mounting plates can be compatible with one or more of the following: average value articulators, semi-adjustable articulators, fully-adjustable articulators, full-size articulators, handheld articulators, and other types of articulators. Mounting plates can be temporarily or permanently mounted to these articulators. Some embodiments of mounting plates may be configured to be removably coupled to one or more of the different types of articulators. For example, one type of mounting plate may be configured to be removably coupled, such as by threading, snap fits, or magnets, to both hand-held and full-size articulators.

One embodiment of a dental articulator is sized to fit comfortably within a user's hand so that the user can easily hold and manually work with the dental articulator. The dental articulator can be easily picked up and manipulated by a user. The dental articulator is preferably a handheld, portable articulator; however, the dental articulator can also be used on a support surface.

In some variations, the upper mounting plate has at least one indicium that can be used for vertical alignment. In some variations, the lower mounting plate has at least one indicium that can also be used for vertical alignment. The indicium can comprise at least one of printing, a structure member (e.g., a rib, truss, etc.), or other visually distinct indicium. In some embodiments, the plates have at least one vertically extending indicium for alignment.

In some embodiments, an upper mounting plate is connected to an upper dental cast by using mounting plaster or stone. The upper mounting plate is coupled to one end of the upper member of the articulator frame. A lower mounting plate is connected to a lower dental cast by using mounting plaster or stone. The lower mounting plate is coupled to one end of the elongate lower member of the articulator frame. The dental articulator is sized so as to fit comfortably within a user's hand so that the user can easily hold and manually work with the dental articulator.

In some embodiments, the articulator frame has the lower member having a curved portion. The lower member can be substantially V-shaped as viewed from the side. In some variations, the lower member may include one or more elongate members. The elongate members can have substantially rectangular axial cross-sections. In some embodiments, the lower member has a width that is greater than its thickness. The elongate members can also have other shapes.

In some embodiments, the axis of rotation of the dental articulator is positioned higher than a lower portion of the upper dental cast when the dental articulator is in a closed position. In some embodiments, the axis of rotation is positioned higher than a substantial portion of the upper dental cast when the dental articulator is in a closed position.

In some embodiments, the articulator frame is sufficiently flexible so as to permit lateral and protrusive (backward or forward) movement of the upper dental cast with respect to the lower dental cast. In some embodiments, the articulator frame is made of plastic, metal, or other suitable material. In some embodiments, the articulator frame comprises one or more reinforcement ribs, gussets, or trusses for increasing stiffness of the articulator frame.

In some embodiments, a method of simulating human jaw movement is provided. The method comprises coupling an upper dental cast and a lower dental cast to a full-size dental articulator such that the upper and lower dental casts rotate about an axis that substantially corresponds to a hinge axis of a patient from which the upper and lower casts were made and related. The upper and the lower dental casts are removed from the full-size dental articulator. After removing the upper and lower dental casts from the full-size dental articulator, the upper dental cast and the lower dental cast are coupled to a handheld dental articulator. In some variations, the upper and lower dental casts can be removed from the handheld articulator. The upper and lower dental casts are then coupled back on the full-size articulator. In some variations, the handheld dental articulator and the full-size dental articulator may also define similar axes of rotation.

Another method may comprise coupling an upper dental cast and a lower dental cast to a handheld dental articulator such that the upper and lower dental casts rotate about an axis that substantially corresponds to a hinge axis of a patient from which the upper and lower casts were made and related. The upper and the lower dental casts are removed from the handheld dental articulator. After removing the upper and lower dental casts from the handheld articulator, the upper and the lower dental casts are coupled to a full-size dental articulator. In some variations, the upper and lower dental casts can be removed from the full-size articulator. The upper and lower dental casts are then coupled back on the handheld articulator. In some variations, the handheld dental articulator and the full-size articulator may also define similar axes of rotation.

In some variations, the upper dental cast and the lower dental cast are removed from the full-size dental articulator. The upper and lower dental casts are then coupled to a handheld dental articulator. In some variations, the handheld dental articulator and the full-size articulator define substantially similar paths of travel of the upper and lower dental casts when the casts are articulated. In some variations, the handheld dental articulator and the full-size articulator define similar axes of rotation. In some variations, the upper dental cast is coupled to the handheld dental articulator by coupling an upper mounting plate, which is holding the upper dental cast, to an upper member of the handheld dental articulator. The lower dental cast is coupled to the handheld dental articulator by coupling a lower mounting plate, which is holding the lower dental cast, to a lower, elongated member of the handheld dental articulator. In some variations, the upper and lower dental casts are coupled to the full-size dental articulator by coupling the upper and lower mounting plates, which are attached to the upper and lower dental casts, to an upper arm and a lower arm, respectively.

One embodiment of the present invention is a handheld dental articulator comprising an articulator frame comprising an upper member and a lower member. The articulator frame has a pivot axis connecting the upper member to the lower member. An upper mounting plate configured to hold an upper dental cast is connected to the upper member, and a lower mounting plate configured to hold a lower dental cast is connected to the lower member. The pivot axis is higher than a lower portion of the upper dental cast when the articulator is in a closed position. In one embodiment, the pivot axis is positioned higher than a substantial portion of the upper dental cast. In another embodiment, the pivot axis is substantially parallel and horizontal with the upper mounting plate. The articulator frame may extend behind a location of the upper and lower dental casts in a vertical plane extending through the upper and lower mounting plates.

In another embodiment of the present invention, a dental articulator comprises an upper mounting plate configured to be connected to an upper dental cast and a lower mounting plate configured to be connected to a lower dental cast. The upper mounting plate has a first attachment mechanism configured to be removably coupled to a first end of a handheld articulator frame, and a second attachment mechanism configured to be removably coupled to a first portion of a full-size articulator. The lower mounting plate has a first attachment mechanism configured to be removably coupled to a second end of a handheld articulator frame, and a second attachment mechanism configured to be removably coupled to a second portion of a full-size articulator. The first attachment mechanism of the upper and lower mounting plates may comprise a snap fitting, and the second attachment mechanism of the upper and lower mounting plates may comprise a magnetic connection.

Another embodiment of the present invention provides a dental articulator system comprising a handheld articulator and a full-size articulator. The handheld articulator has upper and lower mounting plates and an articulator frame. A pivot axis of the handheld articulator pivots the upper mounting plate relative to the lower mounting plate. The full-size articulator has an upper frame and a lower frame, and a hinge axis to pivot the upper frame relative to the lower frame. The hinge axis substantially corresponds to a hinge axis of a patient. The upper and lower mounting plates of the handheld articulator are removably connectable to the upper and lower frames of the full-size articulator to allow rotation of the upper and lower mounting plates about the hinge axis that substantially corresponds with the hinge axis of a patient. The pivot axis of the handheld articulator substantially corresponds with the hinge axis of the full-size articulator.

Another embodiment of the present invention provides a method of simulating human jaw movement. An upper mounting plate coupled to an upper dental cast and a lower mounting plate coupled to a lower dental cast are provided. The upper and lower mounting plates are removably coupled to a first dental articulator. The upper and lower mounting plates are removed from the first dental articulator. The upper and lower mounting plates are removably coupled to a second dental articulator.

BRIEF DESCRIPTION OF THE DRAWINGS

FIG. 21A is a bottom elevational view of a mounting plate of a full-size articulator for connecting to the mounting plates of the articulator assembly of FIG. 4.

FIG. 21B is a side elevational view of the mounting plate of FIG. 21A.

FIG. 21C is a top elevational view of the mounting plate of FIG. 21A.

FIG. 21D is a cross-sectional view of the mounting plate of FIG. 21A taken through a groove of the mounting plate.

DETAILED DESCRIPTION OF THE PREFERRED EMBODIMENTS

Figure 1:
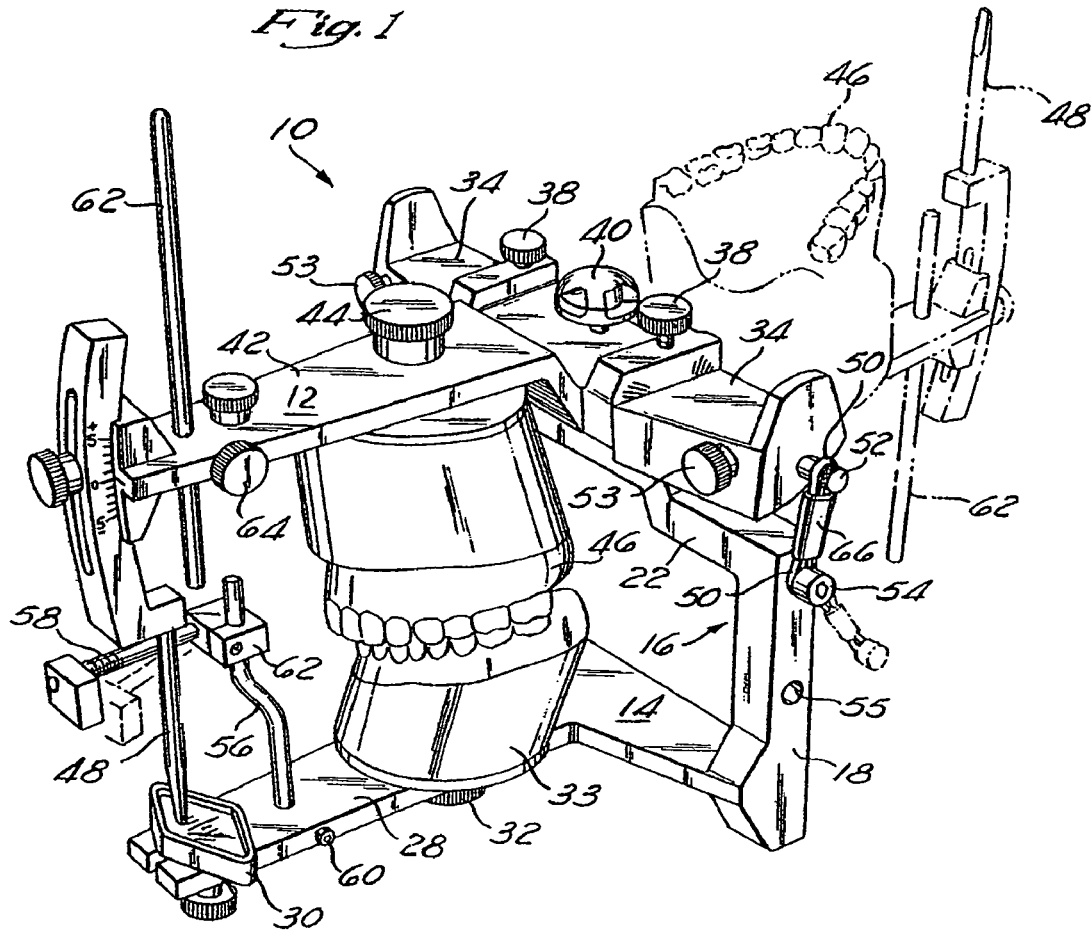
FIG. 1 is a perspective view of a dental articulator system.

Generally, full-size dental articulators often have the ability to simulate closely the actual centric, lateral, and protrusive jaw movements of the patient in order that the prosthodontist may produce a comfortable and effective dental prosthesis. FIG. 1 illustrates one embodiment of a full-size articulator 10. An upper dental cast and a lower dental cast can be mounted to a full-size dental articulator such that the upper and lower dental casts rotate about an axis that substantially corresponds to a hinge axis of a patient from which the upper and lower casts were made and related. The upper dental cast and the lower dental cast can be removed from the full-size dental articulator. After removing the upper and lower dental casts from the full-size dental articulator, the upper dental cast and the lower dental cast are coupled to a handheld dental articulator, such as the handheld dental articulator 100 illustrated in FIG. 4. The handheld dental articulator can also be used to simulate closely the actual centric, lateral, and/or protrusive jaw movements. In some variations, the upper and lower dental casts can then removed from the handheld dental articulator. The upper and lower dental casts can then be coupled back on the full-size articulator. The full-size articulator and the handheld articulator can be used for occlusal/occlusion diagnosis, developing a treatment plan, constructing prostheses, acquiring base line records, communicating with laboratories, didactics, prosthesis fabrication, and the like.

With reference to FIG. 1, a dental articulator 10 that simulates jaw movement of a patient is illustrated. The articulator 10 is an arcon-type articulator of the same general type as is disclosed in U.S. Pat. No. 4,209,909, to Robert L. Lee, the disclosure of which is hereby incorporated by reference. The articulator 10 is configured to rest upon a support surface while an upper frame 12 is moved between a closed position and an open position and other positions of jaw movement.

Figure 3:
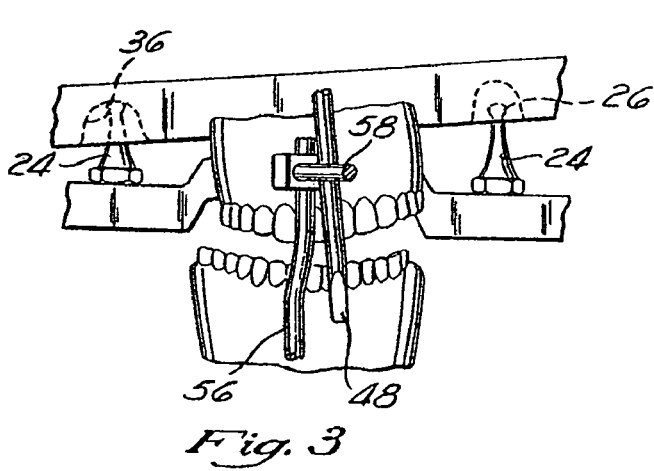
FIG. 3 is a partial front elevational view showing use of a locator rod in conjunction with an incisal pin of the dental articulator system of FIG. 1.

The articulator 10 includes the upper frame 12 and a lower frame 14. Both the upper frame 12 and the lower frame 14 are generally T-shaped. The lower frame 14 also has a closed loop vertical frame member 16 having two vertical posts 18 joined at their upper end by a lateral truss 22. The lateral truss, at either end, carries a pair of styluses or condyles 24. As shown in FIG. 3, the condyles 24 are vertically-extending posts with generally spherical elements 26 on their upper ends.

With reference again to FIG. 1, the lower frame 14 has a forward arm 28 supporting an incisal pin rest pad 30 at the forward end thereof. The forward arm 28 also has a mounting screw 32 to which any desired dental model or cast 33 of the lower teeth of a patient may be mounted. The illustrated dental cast 33 includes a dental cast mounted to a mounting plate. The mounting plate is coupled to the lower frame 14 by mounting screws 32.

The upper frame 12 is provided with a pair of guide blocks 34 on either side of the rear portion of the articulator upper frame 12. The guide blocks 34 are provided with a recessed guide surface 36, shown in phantom in FIG. 3. The recessed guide surface 36 pivotally and slidably receives the condyles 24 so that the upper frame 12 can pivot on the condyles 24 on a hinge axis extending through the two spherical elements 26 or slide on the condyles 24 to simulate other movement. The guide blocks 34 are selected and positioned to simulate the jaw movement of the particular patient, and may be removed from the upper frame 12. A pair of guide block adjustment screws 38 may be loosened to permit the guide blocks 34 to be adjusted to a desired position by pivoting them generally about the hinge axis. The guide block adjustment screws 38 can then be locked so as to hold the guide blocks 34 in that desired position.

As disclosed in U.S. Pat. No. 4,209,909, the guide surfaces 36 in the guide blocks 34 engage the condyles 24 to permit sliding and pivoting movement that mimics or simulates the movement of the human jaw. Accordingly, the guide blocks 34, together with the upper frame 12, may slide forward and back, side to side, and may pivot on the condyles 24. Generally, the most deeply recessed portions of the guide surfaces 36 correspond to the hinge position or centric position; that is, the position of the human jaws in which the lower jaw is fully seated and centered in the skull. By sliding the guide blocks 34 rearwardly on the condyles 24, protrusive movement of the human jaw is simulated. Lateral movement of the upper frame 12 in relation to the lower frame 14 simulates lateral side shift and lateral twisting movement of the human jaw. Other arrangements can also be used to simulate jaw movements.

The upper frame 12 may advantageously be provided with a centric pin 40. When depressed, the centric pin 40 enters a slot (not shown) on the lateral truss 22 and holds the articulator frames 12, 14 in the centric position.

An upper forward arm 42 on the upper frame 12 is juxtaposed over the lower forward arm 28 on the lower frame 14. The upper forward arm 42 extends forward from between the guide blocks 34. An upper mounting screw 44 on the upper forward arm 42 is provided for attaching a mounting plate, which holds an upper dental cast 46. The illustrated upper dental cast 46 includes a dental cast mounted to a mounting plate.

An incisal rest pin 48 is attached to the front end of the upper forward arm 42 and extends generally vertically downward (when the articulator 10 is in fully closed position) to the rest pad 30. Indicia are provided on both the incisal pin 48 and the rest pad 30 for indicating the height and transverse position of the incisal pin 48.

A retainer 50 is preferably provided laterally outboard of the condyles 24 connecting the upper frame 12 to the lower frame 14. The retainer 50 biases the upper frame 12 toward the lower frame 14. Any elastic material suitable for performing this function may be used. Examples of suitable materials are metals (in the form of a spring) and elastomeric materials, such as butyl rubber, neoprene rubber, polyurethane, vulcanized natural rubber, nitrile rubber, polysulfide rubber, styrenebutadiene copolymer, isoprene rubber, and silicone rubber. Neoprene rubber having a circular cross-section and formed into a loop is particularly preferred. Other materials can also be used.

An upper pin 52 can be provided on each side of the upper frame 12 on the outward side of the guide blocks 34. It is preferred that the upper pins 52 be coaxial with the hinge axis through the condyles 24 when the articulator is in centric position. The upper pins 52 are held in place with locking screws 53.

A horizontal lower pin 54 is provided on the vertical post 18 of the lower frame 14, preferably directly below the upper pin 52. The retainer 50 extends from the upper pin 52 to the lower pin 54 providing a downward force, biasing the articulator 10 into the centric position. Although the retainer 50 and the pins 52 and 54 are visible in FIG. 1 only on one side of the articulator 10, these same elements are also provided on the opposite side of the articulator 10 so that the condyles 24 are generally between the retainers 50.

If separation of the upper frame 12 from the lower frame 14 is desired, the locking screws 53 are loosened and the upper pins 52 are removed from the upper frame 12. The upper frame 12 can then be lifted off the lower frame 14. For convenience, the upper pin 52 may be inserted in a storage hole 55 on the vertical post 18 when removed from the upper frame 12.

Of course, there are a number additional of ways of connecting the upper frame 12 to the lower frame 14 with a retainer 50. Other suitable structures, such as hooks, screws, notches, or appropriate protuberances or recesses may be provided on the upper frame 12 and the lower frame 14 for holding the ends of the retainer 50.

An eccentric positioner or locator pin 56 is provided on the forward arm 28 of the lower frame 14. The locator pin 56 extends generally vertically upward from the forward arm 28. Attached to the locator pin 56 and extending generally horizontally forward therefrom is an eccentric positioner or rod 58. The eccentric positioner rod 58 may be moved into contact with the incisal pin 48 by pivoting the rod 58 around the pin 56, or by pivoting the pin 56. In a preferred embodiment, the locator pin 56 is inserted into a hole in the forward arm 28 and is secured in place with a set screw 60. Likewise, a set screw 62 may be used to secure the locator rod 58 to the locator pin 56.

It is preferred that the locator rod 58 be offset from the center of the articulator 10 by the radius of the incisal pin 48 so that the incisal pin 48 may slide against the locator rod 58 during protrusive movement. Indicia on the locator rod 58 indicate the extent of protrusive displacement from the centric position.

The dental articulator 10 has the significant advantage that it may be fully opened. In other words, the upper frame may pivot from the fully closed position illustrated in solid figure in FIG. 1 through approximately 180° to the fully opened position shown in phantom. In the fully opened position, the upper frame is supported by the retainers 50 and by a support rod 62 extending generally vertically through the upper forward arm 42 of the upper frame 12. The support rod 62 may be a part of the incisal pin 48, or may be a separate structure as shown. An adjustment screw 64 is tightened against the support rod 62 to maintain it in position and to permit vertical adjustment of the support rod 62.

Figure 2:
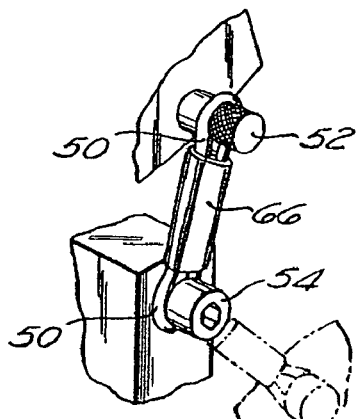
FIG. 2 is a close up perspective view of the dental articulator system of FIG. 1.

In pivoting the upper frame 12 from the fully closed to the fully opened position, the upper frame 12 pivots through about 80° on the hinge axis through the spherical elements 26 of the condyles 24. As the angle between the upper frame 12 and the lower frame 14 approaches 70° or 80° the condyles 24 begin to leave the guide blocks 34. The upper frame 12 continues to pivot through the remainder of 180° with the retainers 50 serving as hinges or supports. In the fully opened position, the guide blocks 34 of the upper frame 12 are supported by the retainers 50 as shown in phantom in FIG. 2.

With regard to the pivoting motion of the upper frame 12, the retainer 50 can be situated as to provide no elastomeric resistance to pivoting motion throughout its movement. At the same time during the initial 0° to 80° to 90° of opening motion the retainer 50 provides a strong force to bias the frames into engagement, and more particularly, into the centric position. This is made possible by locating the retainer 50 on or around the hinge axis by placing the upper pins 52 in coaxial relationship on the hinge axis extending through the condyles elements 26 when the articulator 10 is in the centric position.

The articulator 10 is continually biased into a centric position by the retainers 50 during the jaw simulator movement, and yet can freely pivot from a fully closed to a fully opened position. Pivotal motion is facilitated by making the retainer 50 circular in cross-section so that the pin 52 may freely rotate in the retainer 50. Such rotation may be enhanced by lubricating the retainer 50 or forming the retainer 50 of a self-lubricating material. To obtain this movement, it is not essential that the retainer 50 be located laterally outboard of the condyles 24, so long as it may pivot about the hinge axis to avoid elastic resistance to opening and closing motion. The placement of the retainer 50 laterally outboard of the condyles 24 presents significant advantages. One such advantage is in leverage: a retainer outboard of the condyles can retain the condyles elements 26, 36 in the guides much more effectively and positively than can a retainer between the condyles 24. In addition, a pair of outboard retainers 50 is more certain to deliver a balanced biasing force and functions more effectively as a hinge.

Another significant advantage of the illustrated articulator 10 may be realized by providing a stiff tubular sleeve 66 on the retainer 50 and forming the retainer 50 into a loop. Thus, as is most clearly illustrated in FIG. 2, the sleeve 66 is placed on the retainer 50 so that a loop of retainer 50 extends from either end of sleeve 66. The sleeve 66 has two important functions. First, it forms a relatively small loop in each end of the retainer 50, thus facilitating retention of the retainer 50 on the pins 52 and 54. In addition, the sleeve 66 provides the retainer 50 with rigidity. This rigidity contributes significantly to the efficacy of the retainer 50 as a hinge when pivoting the upper frame 12 to the fully opened position. It also serves as a separator by maintaining separation between the upper frame 12 and the lower frame 14 during such pivoting motion, providing smooth pivoting motion and preventing bothersome and potentially damaging contact between the two frame pieces. The sleeve 66 may be made of any material having sufficient rigidity to maintain separation between the upper frame 12 and the lower frame 14 during pivoting motion. Suitable materials include metal and plastic, and preferably resilient plastic or rubber tubing. Of course, the sleeve could be an integral part of the retainer itself.

Not only does the illustrated articulator 10 facilitate the study of dental casts in the centric position, it also permits accurate and repeatable location and maintenance of whatever non-centric position the prosthodontist desires to study. This is done, as illustrated in FIG. 3, through use of the eccentric positioner 58. In FIG. 3, the positioner or locator rod 58 is holding the incisal pin 48 to maintain the articulator 10 in a non-centric position. The condyle 24 on the right in FIG. 3 has not left the guide surface 36. Rather, as is explained in U.S. Pat. No. 4,209,909, the guide surface 36 slopes so that the spacing between the frames 12 and 14 increases when the condyle 24 moves out of the centric position of the guide surface 36. In addition, the spacing between the dental casts in FIG. 3 is exaggerated; in ordinary use, some or all the teeth would be in contact.

In a preferred embodiment, the set screws 60 and 62 are tightened sufficiently to retain the eccentric locator or positioner rod 58 and locator pin 56 in any desired position against the centering pressure of retainers 50 and yet permit an operator to pivot the locator rod 58 (as shown in phantom in FIG. 1) to a new position without loosening the set screws 60 and 62. It is further preferred that the locator pin 56 be offset or bent away from the dental casts 33, 46 to permit a greater range of movement and positions for locator rod 58 and also to provide adequate clearance for the prosthodontist to work on the dental casts 33, 46.

The locator rod 58 may also be used as a reference for repeatable non-centric position of the articulator 10. Indicia provided on the locator rod 58 can be used to indicate the extent of protrusive movement. In addition, other non-centric movements may be accurately repeated by positioning the locator rod 58 and then moving the articulator upwardly until the incisal pin 48 contacts the locator rod 58. It should also be noted that proper positioning of the locator rod 58 alongside the incisal guide pin 48 permits the user to effect pure protrusive movement without side components.

The articulator 10 is designed to remain on a support surface while the user opens and closes the articulator 10. Thus, the lower frame 14 of the articulator 10 remains stationary as the upper frame 12 is articulated by rotating the upper forward arm 42. During the prosthetic fabrication process, the articulator 10 can remain stationary on a support surface. Although a user can pick up and move the articulator 10, the full-size articulator 10 is not the most suitable for handheld operation.

Figure 4:
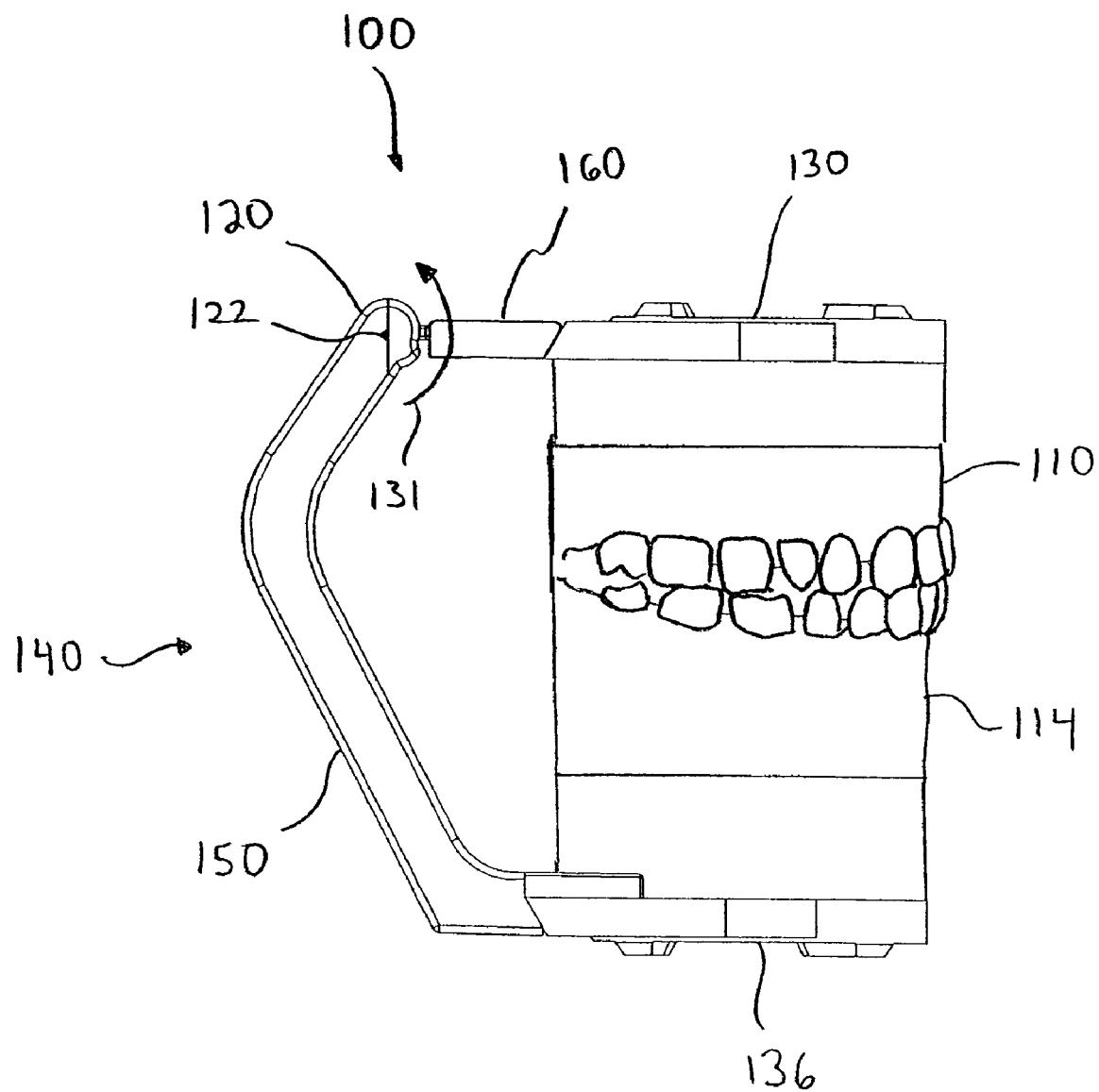
FIG. 4 is a side elevational view of a portable dental articulator assembly in a closed position.
Figure 5:
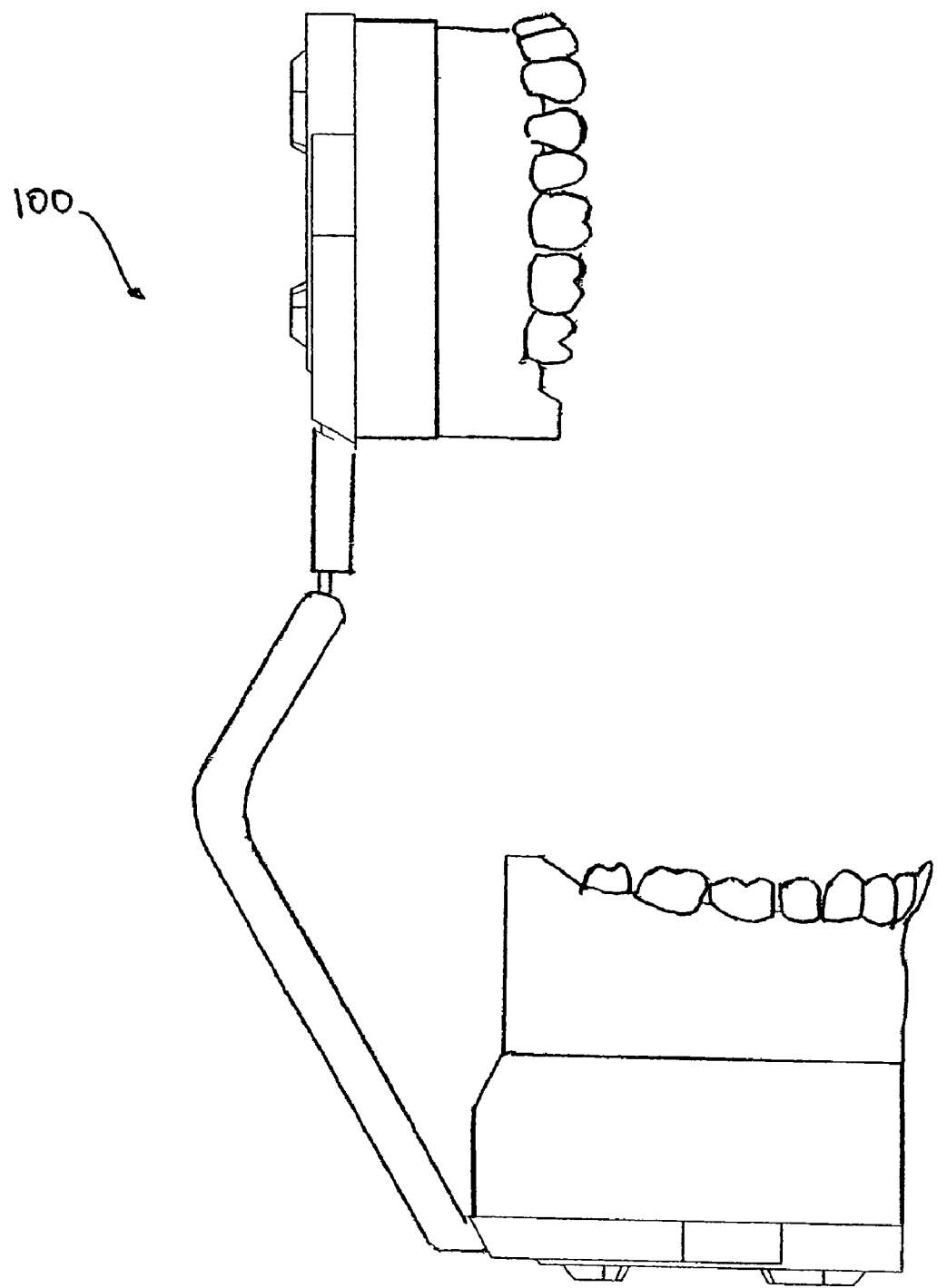
FIG. 5 is a side elevational view of the dental articulator assembly of FIG. 4 in an open position.
Figure 6:
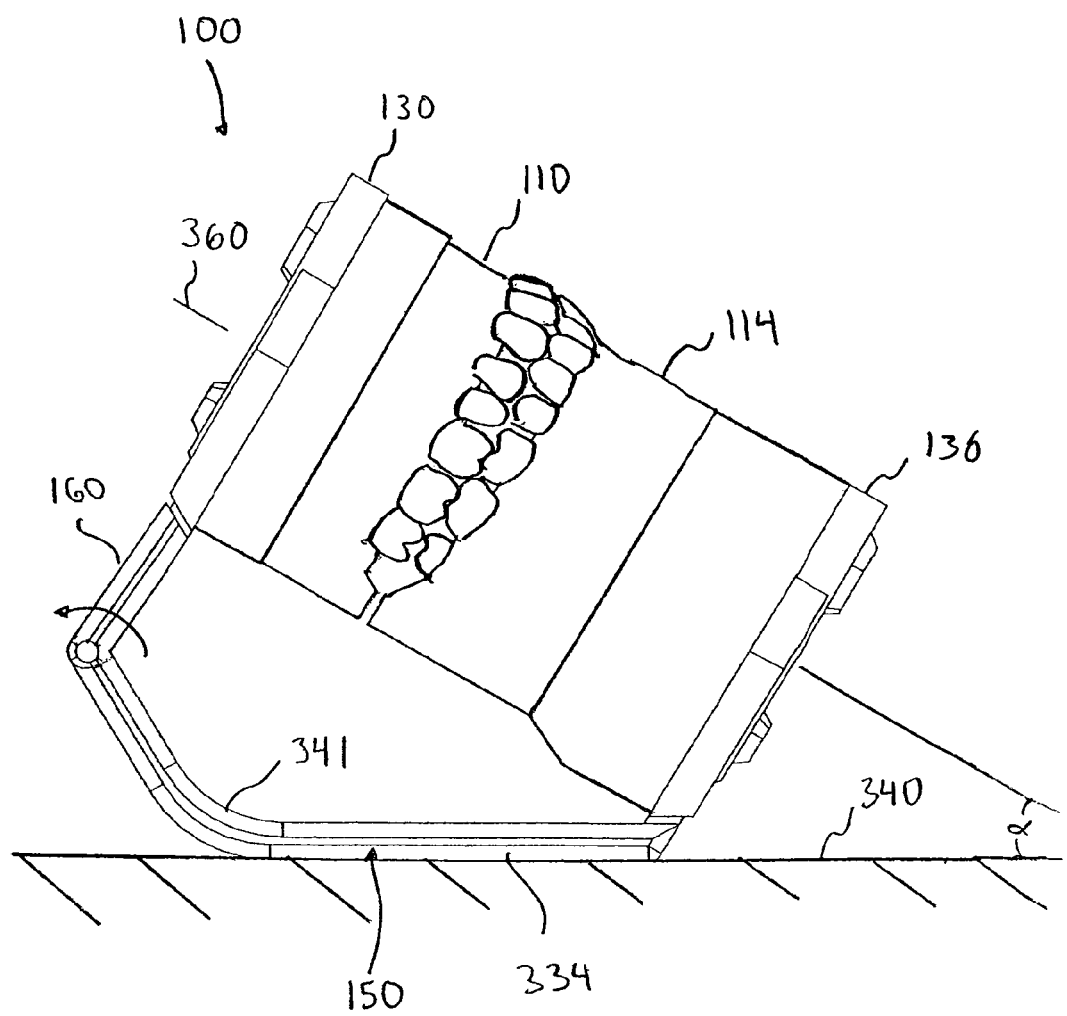
FIG. 6 is a side elevational view of the dental articulator assembly of FIG. 4 resting upon a support surface.

FIGS. 4 to 6 are side elevational views of a dental articulator assembly for simulating movements of a jaw. An upper dental cast 110 and a lower dental cast 114 are mounted to the articulator assembly 100. The articulator assembly 100 can be moved from the illustrated closed position of FIG. 4 to an open position of FIG. 5 to mimic movement of a patient's jaw. In contrast to the articulator 10 discussed above, the portable or handheld articulator assembly 100 is sized so as to fit comfortably within a person's hand for convenient manipulation. The portable, handheld articulator assembly 100 can be used to perform fabrication techniques the same or different from the fabrication techniques used with a full-size dental articulator. As used herein, the term "portable" means that the articulator assembly 100 can be easily transported by a person and used where convenient. For example, the articulator assembly 100 is small enough to be carried in a person's hand while the person uses their other hand to fabricate dental prostheses. Advantageously, use of a portable or handheld articulator assembly can help reduce wear on a full-size articulator as described above.

To simulate the movement of a human jaw, the illustrated articulator assembly 100 includes a joint 120 that defines a pivot axis 122 (see FIGS. 4 and 7). The axis 122 is preferably an axis of rotation that simulates a patient's jaw movement, preferably simulating an anatomically or statistically accurate axis of rotation. As such, the articulator assembly 100 can be utilized to simulate accurately the movements of a patient's jaw for diagnosis, treatment, treatment planning and/or production of dental prostheses. The articulator assembly 100 is preferably capable of closely simulating the actual concentric jaw movements of a patient so that the prosthodontist may produce a properly sized dental prosthesis. The illustrated articulator assembly 100 can be modified to also simulate lateral and/or protrusive jaw movements. The arrangement of the joint 120 can thus be selected for a desired range or parameters jaw movements.

With continued reference to FIG. 4, the articulator assembly 100 comprises an upper mounting plate 130 and a lower mounting plate 136. The mounting plates 130, 136 are configured to hold the dental casts 110, 114, respectively. In some embodiments, including the illustrated embodiment, the dental cast 110 is a maxillary or upper study cast. The dental cast 114 is a mandibular or lower study cast.

The articulator assembly 100 also includes an articulator frame 140 that is connected to the upper mounting plate 130 and the lower mounting plate 136. The articulator frame 140 includes a curved elongate lower member 150 that extends upwardly from the lower mounting plate 136. The joint 120 rotatably couples an upper member 160 of the articulator frame 140 to the elongate lower member 150. The upper member 160 extends outwardly from the joint 120 and is adapted to hold the upper mounting plate 130. The illustrated upper member 160 is generally parallel to the upper mounting plate 130. The upper member 160 acts as a rotatable arm to permit movement between the upper and lower dental casts 110, 114.

The lower member 150 can have a generally rectangular cross-section taken along a plane perpendicular to the long axis of the lower member 150. The lower member 150 can have a width that is greater than its thickness. The aspect ratio of a cross-section taken along the plane perpendicular to the long axis of the lower member 150 can be greater than about 1, 2, 3, 5, and 7. Other aspect ratios are also possible. The illustrated upper member 160 and lower member 150 have a somewhat rectangular cross-section. The cross-section of the upper member 160 and the lower member 150 can be selected to achieve a desired overall stiffness of the articulator frame 140. The illustrated upper mounting plate 130 is generally horizontally in line with the axis 122, although the mounting plate 130 can be at other positions with respect to the axis 122.

The articulator assembly 100 can provide actual centric, lateral, and/or protrusive jaw movements of the patient. If large lateral jaw movements are desired (i.e., side to side movements), the articulator frame 140 can comprise a somewhat flexible material, such as a flexible polymer. The flexible material permits lateral movement of the articulator frame 140 and associated dental casts 110, 114. One or more reinforcement ribs can be positioned along the articulator frame 140 to adjust the flexibility of the articulator assembly 100 as desired. In some embodiments, however, the articulator frame 140 does not have any reinforcement ribs. Further, the width of the frame 140 (e.g., the width of the upper member 160 and/or lower member 150) can be chosen based on desired structural properties.

The articulator frame 140 can be a disposable frame. As used herein, the term "disposable" when applied to a component, such as the articulator frame 140, is a broad term and means, without limitation, that the component in question is used a finite number of times and then discarded. Some disposable components are used only once and then discarded. Other disposable components are used more than once and then discarded. Some components, such as the mounting plates 130, 136, of the articulator assembly 100 can also be disposable.

FIGS. 7A to 10 illustrate the articulator assembly 100 when it is empty. That is, the dental articulator assembly 100 is illustrated without any dental casts 110, 114. The upper and lower mounting plates 130, 136 are configured to hold maxillary and mandibular study casts 110, 114, respectively.

Figure 7A:
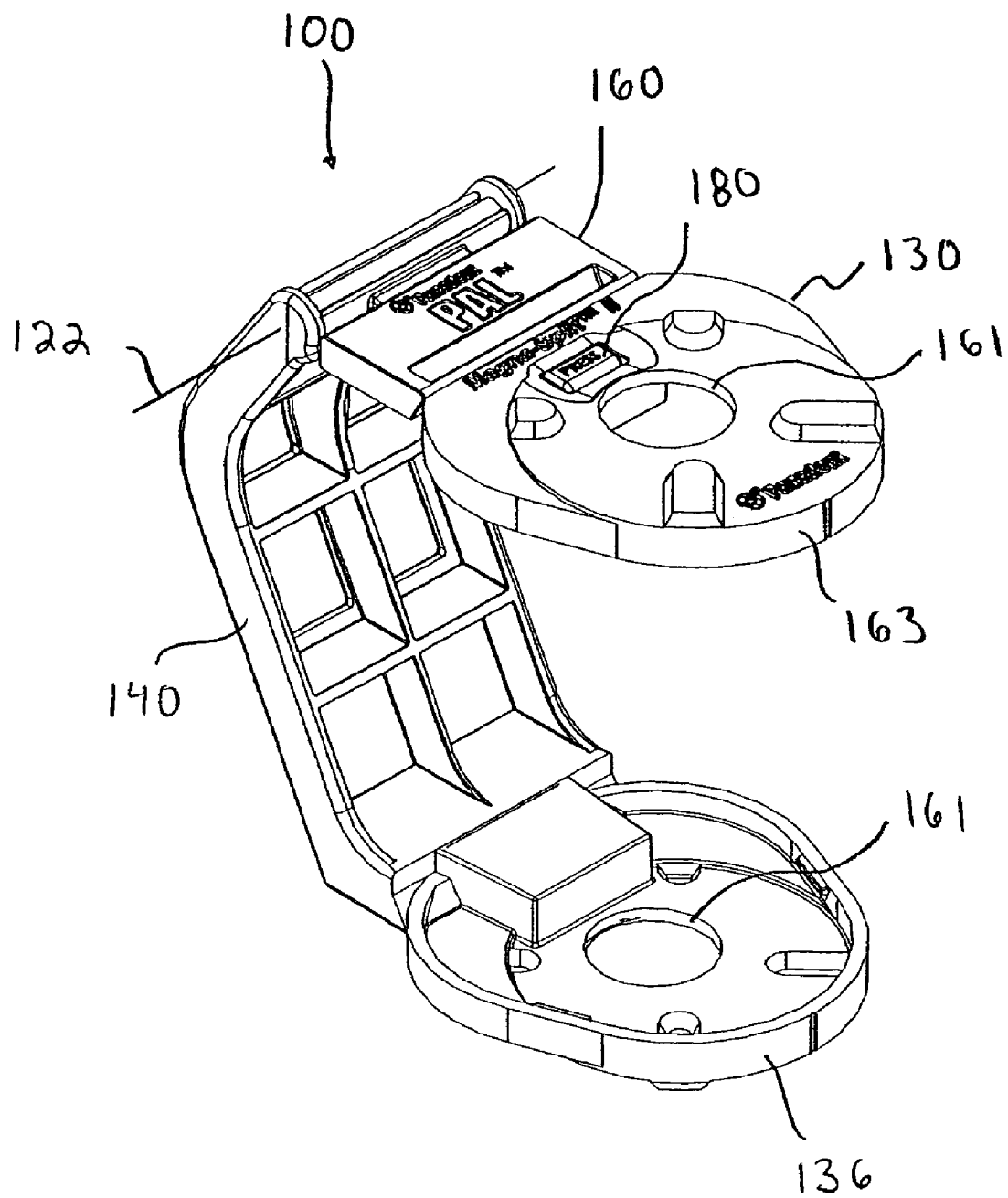
FIG. 7A is a perspective view of the dental articulator assembly of FIG. 4 without dental casts.
Figure 7B:
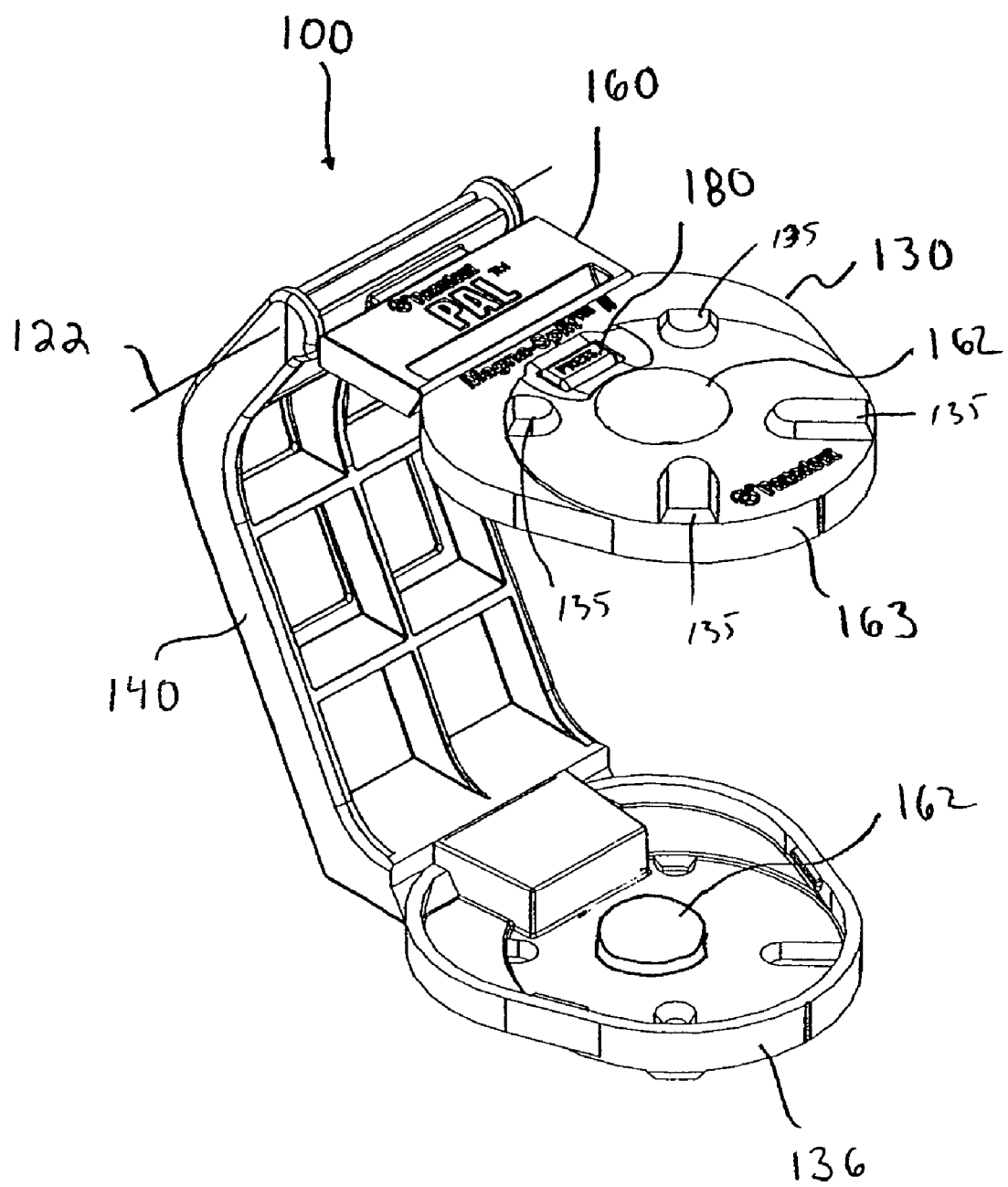
FIG. 7B is a perspective view of the dental articulator assembly of FIG. 7A including metallic inserts.

In the illustrated embodiment of FIG. 7A, the upper and lower mounting plates each comprise an aperture 161 that can hold a coupling element, such as a screw, magnet, magnetic material, metal insert or other structure that can couple the mounting plate 130 to a dental cast and/or an articulator. FIG. 7B illustrates the mounting plates 130 and 136 with a metal insert 162 in each of the apertures 161 adapted for releasably coupling the mounting plates to a full-size articulator as described above, and described further below. In other embodiments, a magnet can be positioned within the aperture 161. The metal insert or magnet can cooperate with a magnet in a dental cast or an articulator to generate a magnetic force sufficient to retain the mounting plate relative to the dental cast or articulator. In one embodiment, where the mounting plates 130, 136 are retained relative to a full-size articulator with magnets, the dental casts may be fixed to the mounting plates with plaster or stone. In some embodiments, the mounting plates 130, 136 comprise a magnet that magnetically couples to a metal (e.g., steel) portion of the articulator. Alternatively, the mounting plates 130, 136 may comprise a metal that couples to a magnetic portion of the articulator, as described further below.

In alternative embodiments, the mounting plates 130, 136 may be connected to a dental cast or articulator with threading. For example, an externally threaded member may extend from the lower surface of the upper mounting plate 130 to threadably mate with an internally threaded hole of a dental cast. The mounting plates may also be internally threaded to receive an externally threaded screw of a dental articulator, as described further below. U.S. Pat. No. 4,600,385 describes various systems, devices, methods, and techniques for mounting dental casts to mounting plates and for connecting mounting plates to a dental articulator. The disclosure of U.S. Pat. No. 4,600,385 is hereby incorporated by reference and made a part of this specification. Adhesive, cements, mounting plaster, mounting stone, couplers, bolts, protrusions, threaded fasteners, mechanical couplers (e.g., nut and bolt assemblies), and/or other coupling means can be used to temporarily or permanently couple dental casts to the mounting plates. Other types of mounting plates can also be used to hold dental casts. In some embodiments, the mounting plates and associated dental casts are configured to couple with mounting screws, such as the mounting screw 44 of FIG. 1.

FIG. 7B illustrates one embodiment of mounting plates 130 and 136 that comprise one or more attachment mechanisms. The attachment mechanisms can couple corresponding mounting plates 130, 136 to a full-size dental articulator, such as the dental articulator 10. For example, the attachment mechanisms can be a metal 162 (e.g., steel) or magnets that couple to magnets or metal of a full-size dental articulator. In such embodiments, the mounting plates 130, 136 can be easily and rapidly mounted and dismounted from the full-size dental articulator. In another example, the attachment mechanism can be a threaded hole that couples to mounting screws 32, 44 of the full-size dental articulator 10.

Figure 8A:
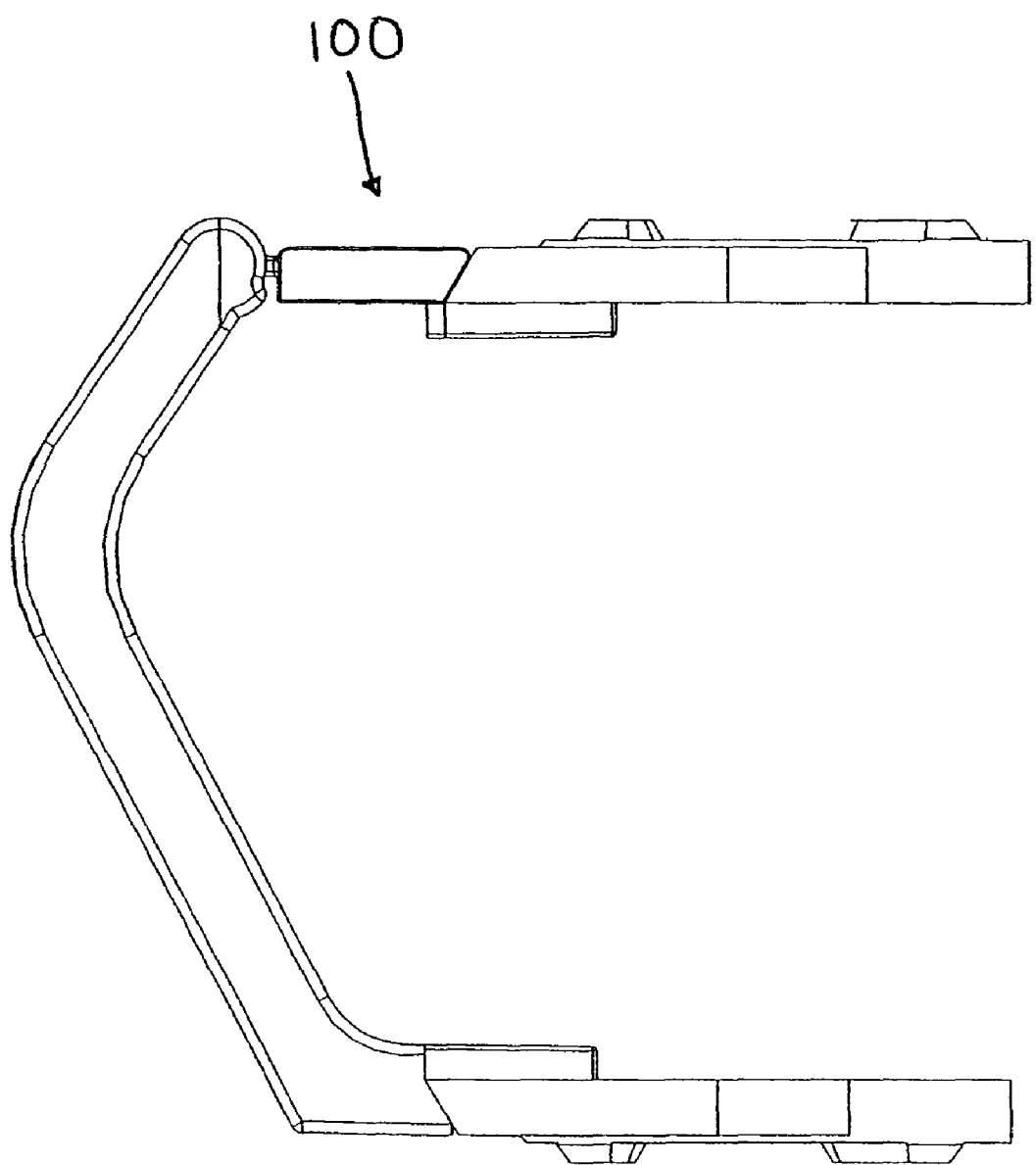
FIG. 8A is a side elevational view of the dental articulator assembly of FIG. 7.
Figure 8B:
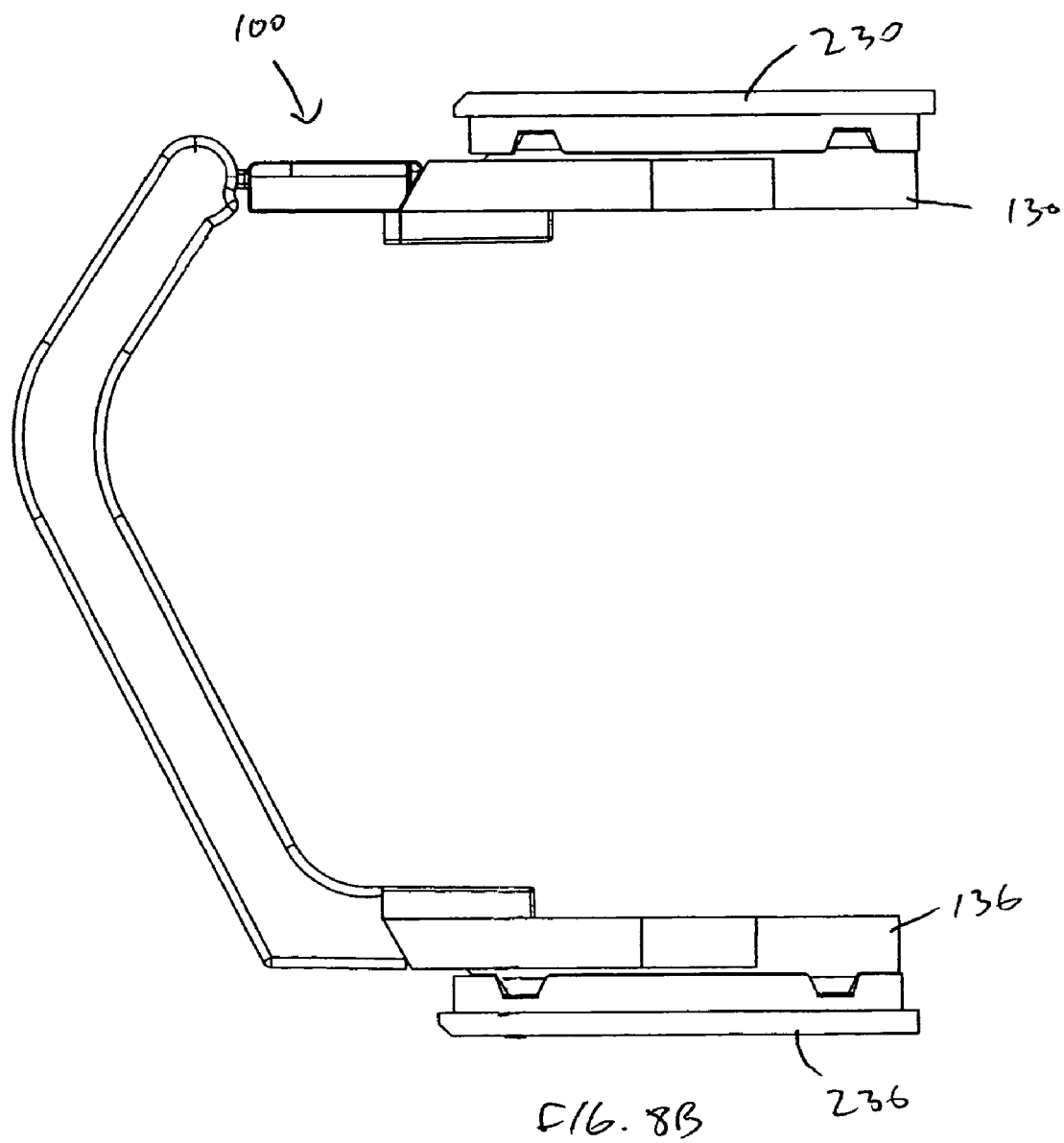
FIG. 8B is a side elevational view of the dental articulator assembly of FIG. 8A with mounting plates connected to mounting plates of a full-size articulator.
Figure 9A:
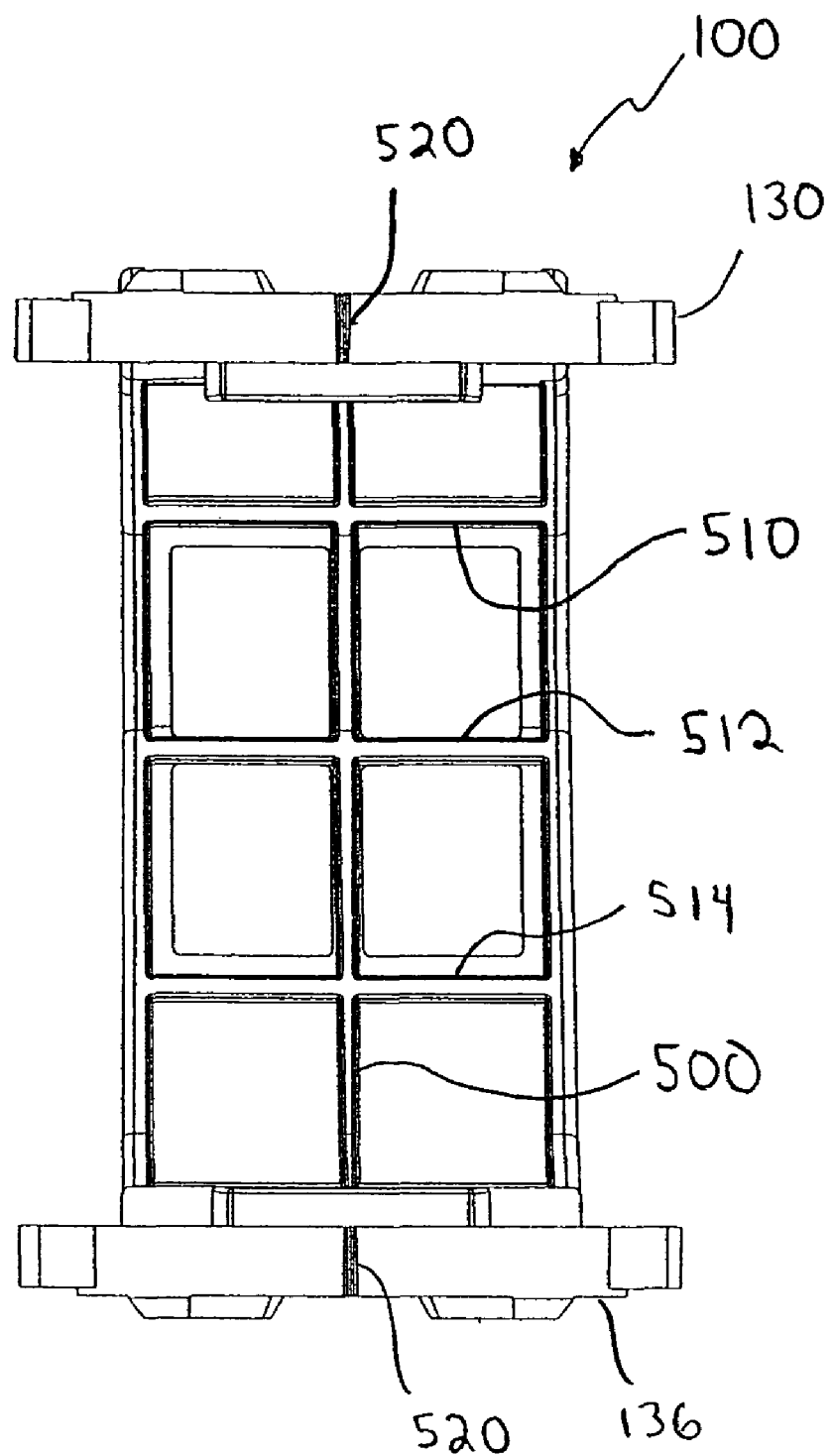
FIG. 9A is a front elevational view of the dental articulator assembly of FIG. 7.
Figure 9B:
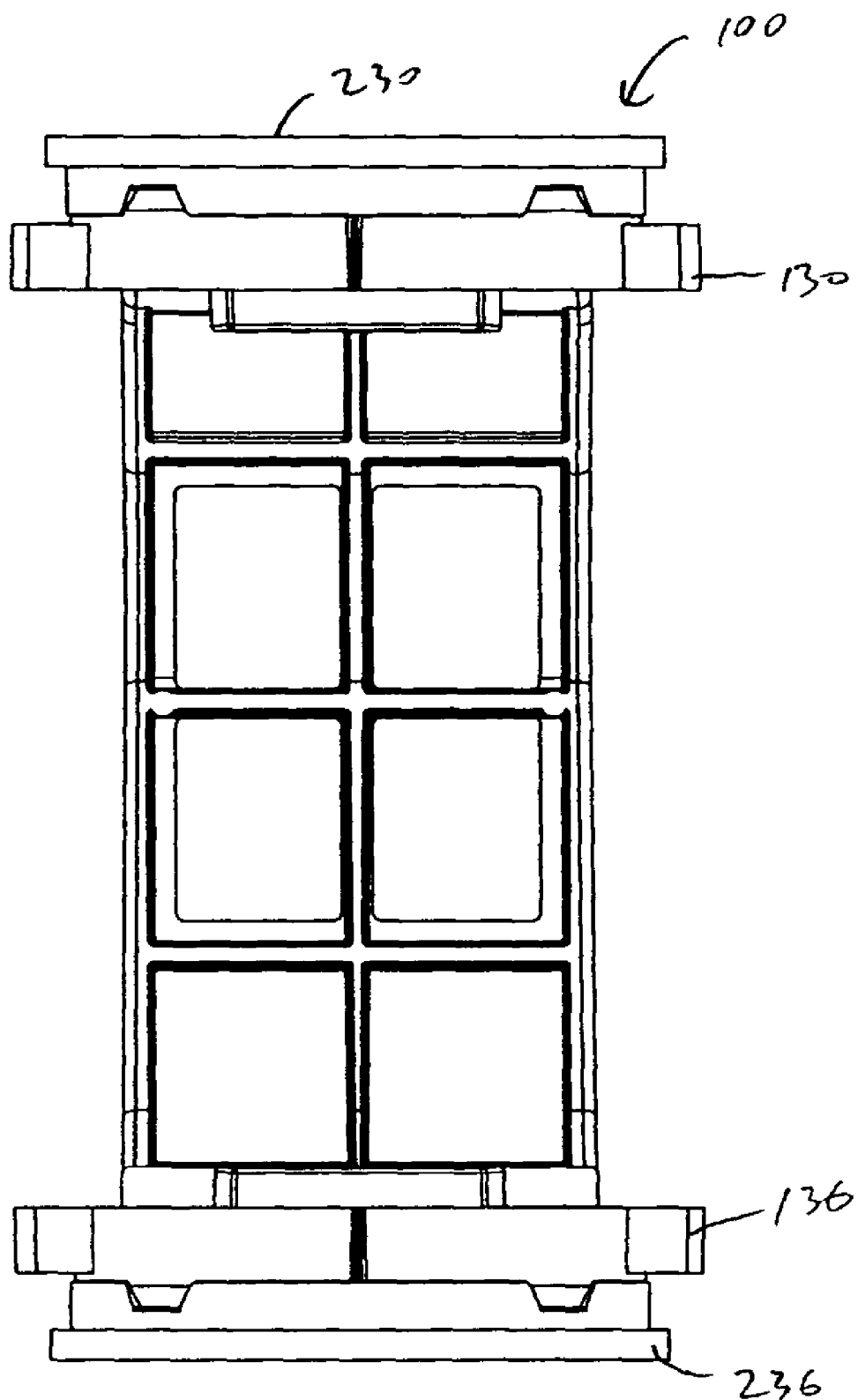
FIG. 9B is a front elevational view of the dental articulator assembly of FIG. 9A with mounting plates connected to mounting plates of a full-size articulator.
Figure 10:
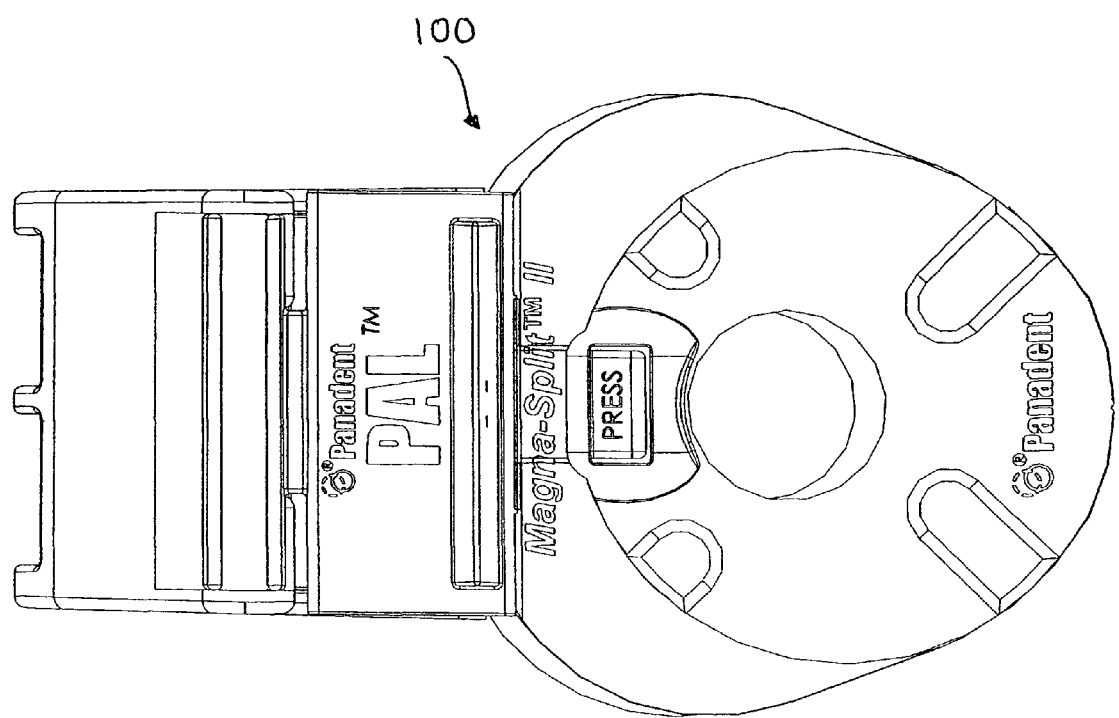
FIG. 10 is a top elevational view of the dental articulator assembly of FIG. 7.
Figure 20:
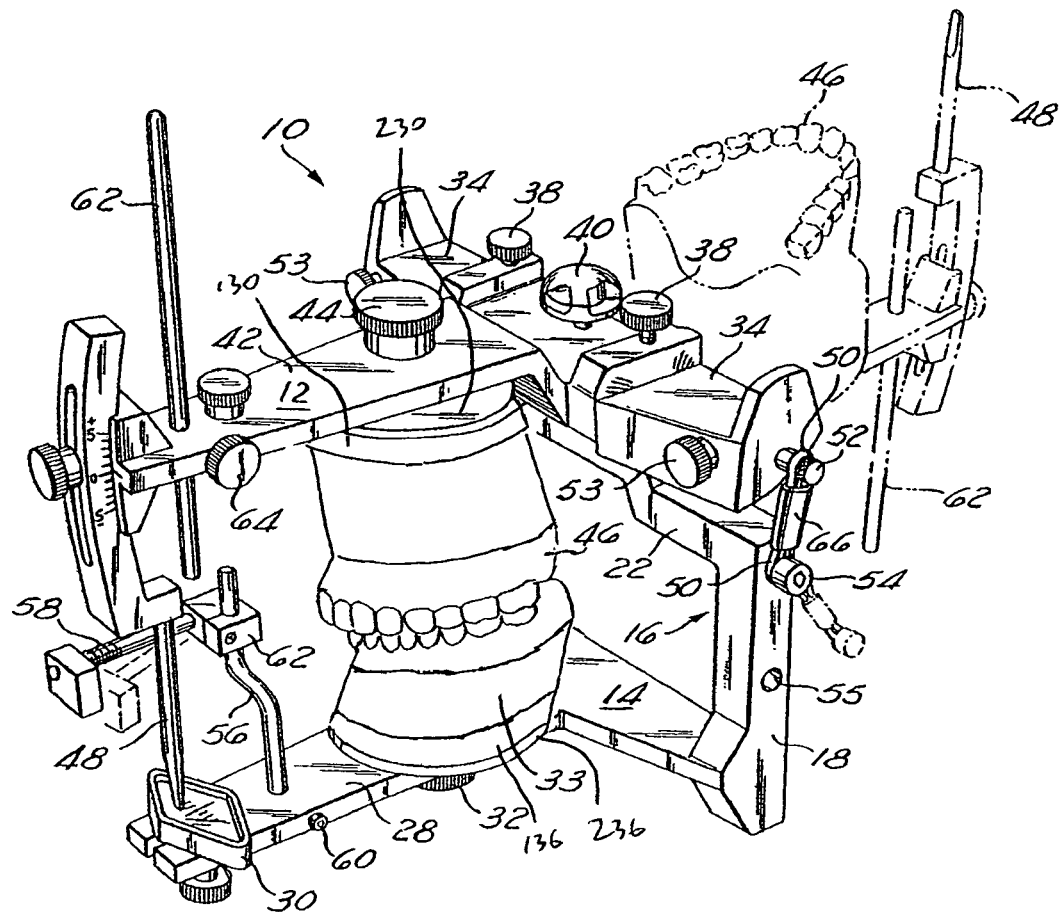
FIG. 20 is a perspective view of the mounting plates of the articulator assembly of FIG. 4 releasably connected to the dental articulator system of FIG. 1.

One embodiment of a preferred connection between the mounting plates 130, 136 and a full-size dental articulator such as illustrated in FIG. 1 is described with respect to FIGS. 8B, 9B and 20. FIGS. 8B and 9B show the articulator assembly 100 connected with the upper mounting plate 130 and lower mounting plate 136. FIG. 20 shows the upper and lower mounting plates 130, 136 connected to the full-size articulator without the articulator frame 140. Each of the mounting plates 130, 136 in this embodiment is in turn connected to mounting plates 230 and 236 which are connected to the full-size articulator such as with mounting screws 44 and 32. Upper mounting plate 230 in one embodiment includes a magnet (not shown) along its lower surface to engage the metal insert 162 of the upper mounting plate 130 to connect the two mounting plates together. Similarly, lower mounting plate 236 preferably includes a magnet along its upper surface to engage the metal insert 162 of the lower mounting plate 136. Alternatively, a standard mounting plate of a full-size articulator may be modified in any suitable fashion for connecting to the mounting plates 130, 136 of the articulator assembly 100, such as with a snap-fitting, clips, threading or other appropriate connection mechanism. As shown in FIGS. 7A and 7B, the upper and lower mounting plates 130, 136 preferably comprise alignment guides or protrusions 135 extending toward the upper or lower mounting plates 230, 236. These alignment guides mate with alignment grooves or recesses on the mounting plates 230, 236 to align the mounting plates 130, 136 relative to the mounting plates 230, 236.

FIGS. 21A-21D illustrate one embodiment of a mounting plate 230 for connecting directly to the full-size articulator. It will be appreciated that the upper and lower mounting plates 230 and 236 may be identical. As shown in the bottom view of FIG. 21A, the mounting plate includes a plurality of grooves 238, which align and mate the mounting plate with the mounting plate 130 or 136. The bottom surface of the mounting plate 230 includes an opening 240 for receiving an insert, such as a steel insert, which may extend from the opening 240 to opening 242 on the top surface of the mounting plate 230. The steel insert may include a magnet (not shown) along the bottom surface, which can magnetically connect with the metal insert 162 of the upper or lower mounting plate 130 or 136. The steel insert may be internally threaded along the top surface for receiving the mounting screw 44 or 32 as shown in FIG. 1. Additional openings 244, 246 and 248 may also be provided for receiving additional screws or alignment protrusions to properly align the mounting plate 230 or 236 relative to the full-size articulator.

Because of the magnetic connection between the mounting plates 130, 136 and the mounting plates 230, 236, a user simply needs to overcome the magnetic force between the plates to remove the plates 130, 136 from the full-size articulator. This may be advantageous over a design where the mounting plates 130, 136 are connected to the full-size articulator by the mounting screws 44, 32, in order to save time. Accordingly, the mounting plates 230, 236 can remain fixed to the full-size articulator, while the mounting plates 130, 136 can be readily removed and reattached as desired.

Figure 12:
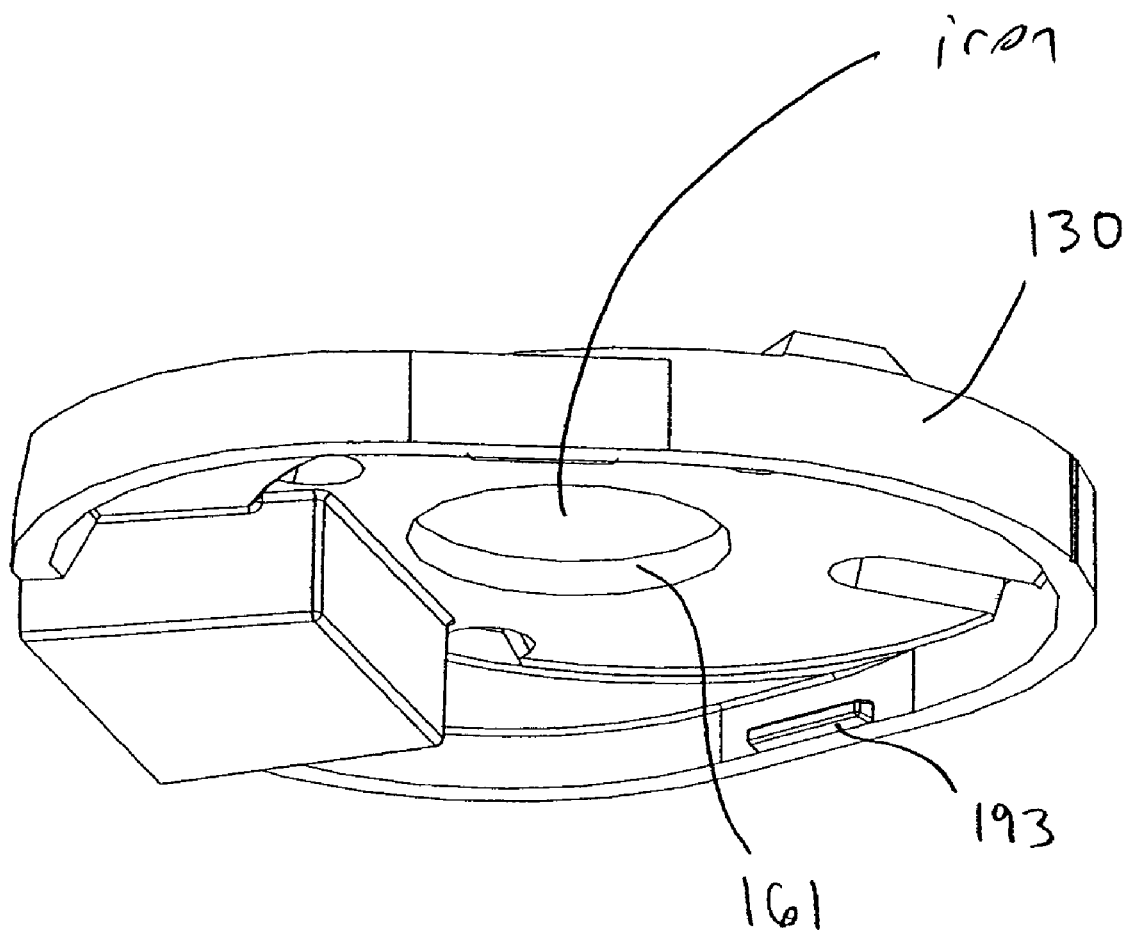
FIG. 12 is another perspective view of the mounting plate of FIG. 11.
Figure 13:
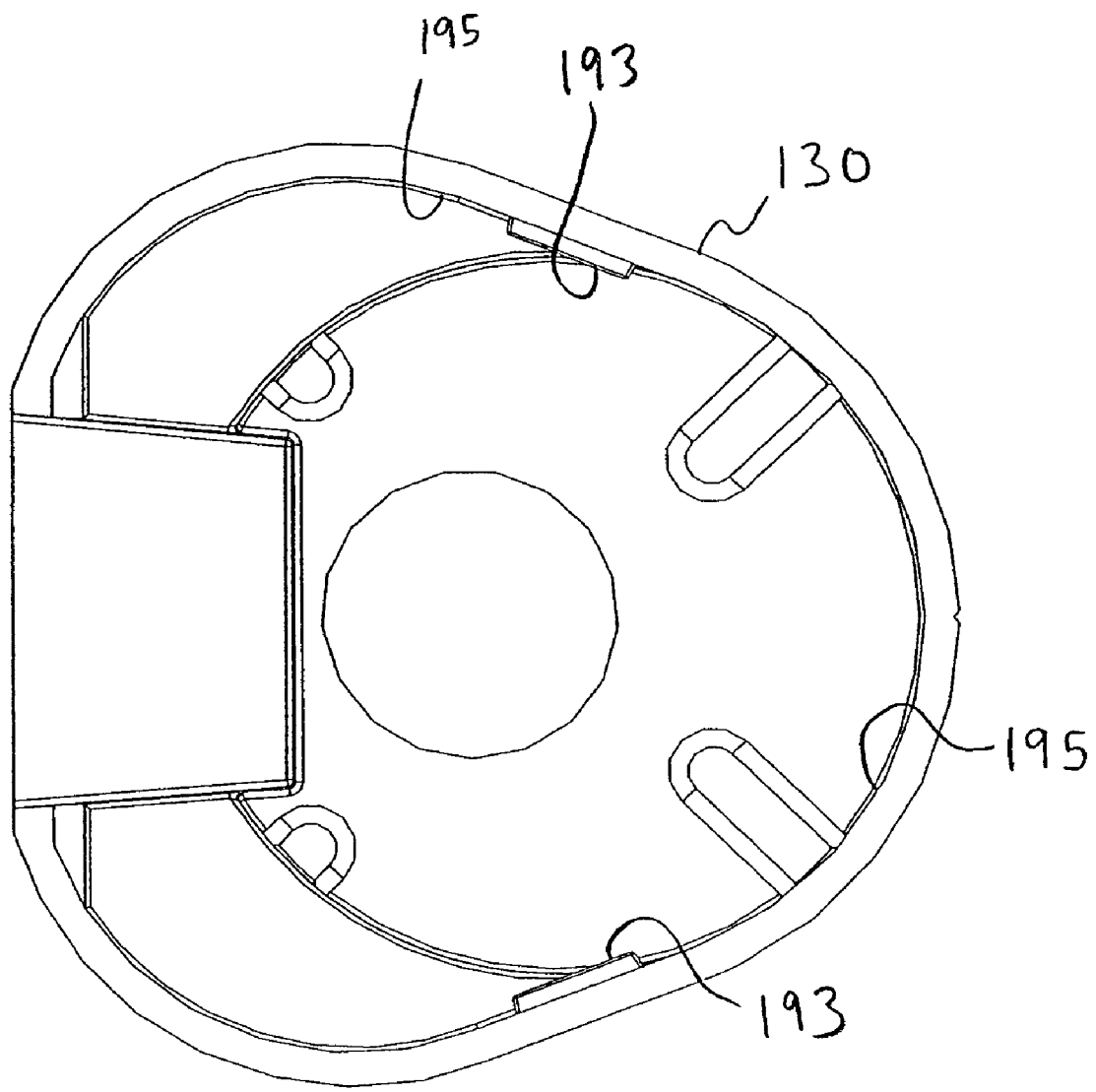
FIG. 13 is a bottom elevational view of the mounting plate of FIG. 11.

As seen in FIGS. 12 and 13, the mounting plate 130 can have a plurality of inwardly extending tabs 193 that cooperate to hold the upper cast 110. If moldable material (e.g., plaster) is placed into the cavity of the plate 130, the tabs 193 can lock the material into the plate 130 once the material has set. In some embodiments, the internal walls 195 of the plate 130 can hold the upper cast 110. The walls 195 can be parallel or angled to one another. The orientation of the walls 195 can help couple the upper cast 110 to the plate 130.

With reference again to FIGS. 7A and 7B, the upper and lower mounting plates 130, 136 can be permanently or temporarily or removably coupled to the articulator frame 140. In some embodiments, including the illustrated embodiment, the mounting plates 130, 136 are temporarily coupled to the articulator frame 140. A release mechanism 180 can be operated to separate the mounting plate 130 from the articulator frame 140. The illustrated release mechanism 180 is a push button that can be depressed to release the upper mounting plate 130 from the articulator frame 140. In this embodiment, the mounting plate 130 can be conveniently attached to or removed from the frame 140 as desired. It will be appreciated that the mounting plates 130 and 136 in one embodiment are identical, and therefore, the description of mounting plate 130 also applies to the mounting plate 136.

Figure 11:
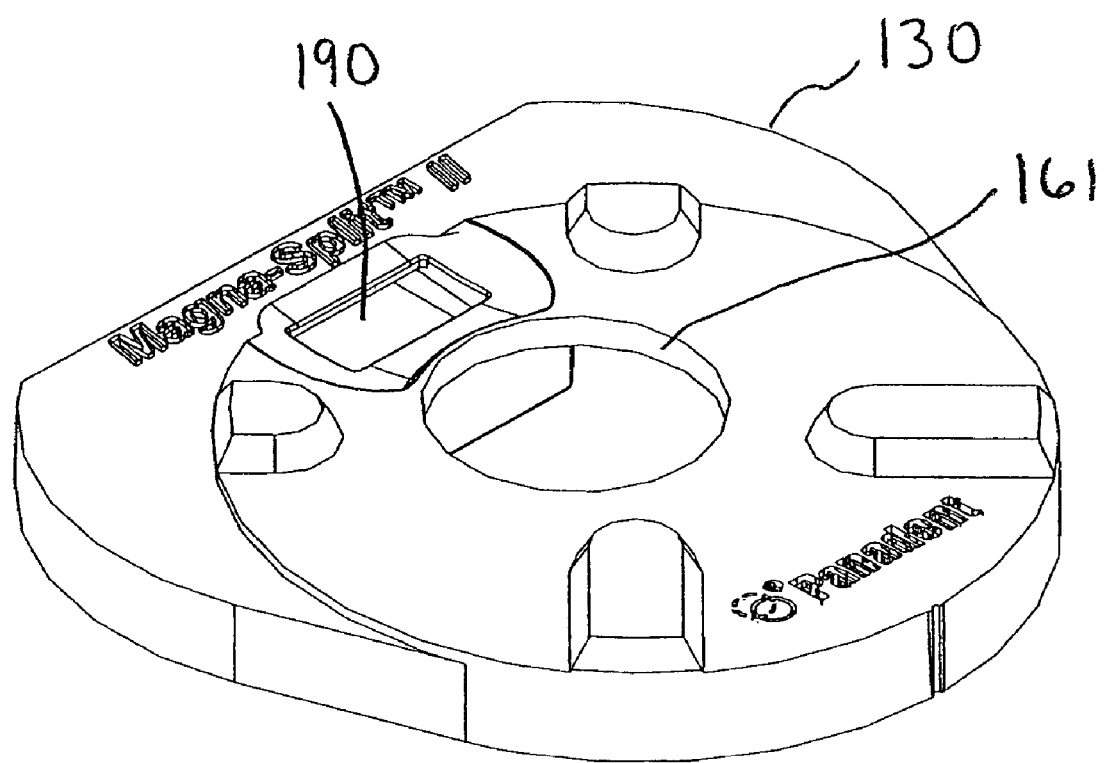
FIG. 11 is a perspective view of a mounting plate for holding a dental cast.

With respect to FIG. 11, an opening or aperture 190 of the plate 130 is configured to receive the push button 180. The opening 190 is positioned along with upper surface of the upper mounting plate 130. When the upper mounting plate 130 is coupled to the articulator frame 140, the push button 180 is preferably exposed through the aperture 190.

Figure 14:
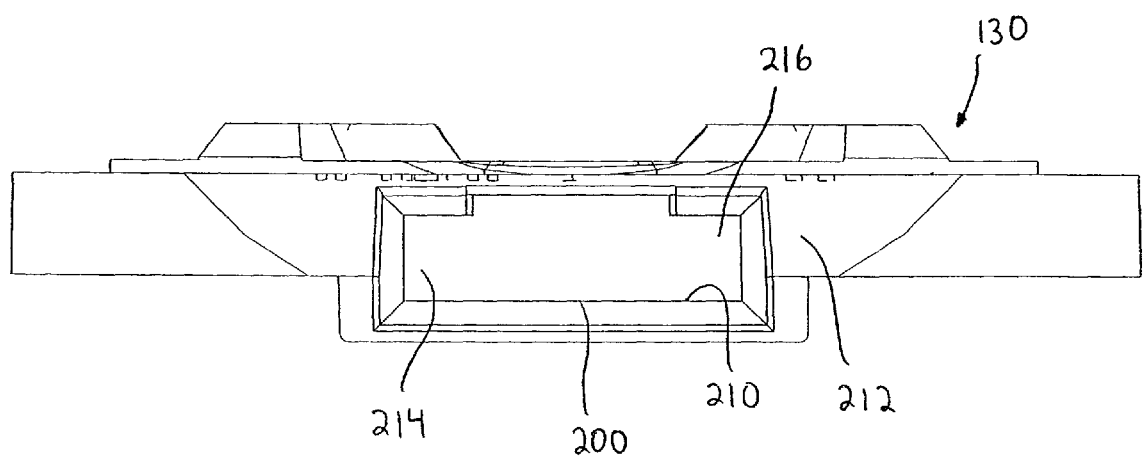
FIG. 14 is a rear elevational view of the mounting plate of FIG. 11.

FIG. 14 illustrates a mounting structure of the upper mounting plate 130. The illustrated mounting plate 130 has a connector port 200 for receiving a portion of the articulator frame 140. The connector port 200 comprises an elongated opening 210 formed along the outer surface 212 of the mounting plate 130. An elongated slot extends inwardly from the opening 210 to form an elongated chamber. The chamber is sized to receive at least a portion of an upper connector 310 of the articulatable frame 140, as described in detail below. It will be appreciated that other types of releasably connections may be used to connect the mounting plates 130, 136 to the articulator frame 140, such as magnets, snaps, adhesives; pins, threading, mechanical couplers, etc.

If desired, the mounting plates 130, 136 can be mounted to various types of articulators. In some embodiments, the mounting plates 130, 136 can be used with both the handheld dental articulator assembly 100 and a full-size dental articulator, such as the dental articulator 10 illustrated in FIGS. 1-3. As such, a user can conveniently mount and dismount the dental cast 110, 114 to different type of articulators to perform different procedures utilizing the same dental casts. A user may thus utilize the articulator assembly 100 to perform some procedures while performing other procedures on a full-size dental articulator. Optionally, the mounting plates 130, 136 can be switched any number of times between the portable dental articulator 100 and the full-size articulator 10 to, for example, fabricate a dental prosthesis. The upper mounting plate 130 can remain coupled to the upper dental cast 110 and the lower mounting plate 136 can remain coupled to the lower dental cast 114 throughout an entire production process.

Although not illustrated, in an alternative embodiment, to mount the upper mounting plate 130 to a full-size articulator, the plate 130 can have a threaded hole that is configured to threadably engage the upper mounting screw 44 of the articulator 10 of FIG. 1. To mount the illustrated mounting plate 130 of FIG. 4 to the articulator 10, the upper mounting plate 130 can be detached from the articulator frame 140. The upper mounting plate 130 and the corresponding upper dental cast 110 can be transferred and positioned along the upper forward arm 42 of the articulator 10. The threaded hole of the upper mounting plate 130 can be positioned to receive the upper mounting screw 44. The screw 44 can be rotated into the threaded hole. In this manner, the upper mounting plate 130 can be coupled to the upper forward arm 42. Similarly, the lower mounting plate 136 can also be mounted to the articulator 10. Various types of mounting plates can be utilized with the articulator assembly 100 to provide compatibility or interchangeability with various types of full-size articulators. For example, the mounting plates can be configured to mount to the full-size articulators disclosed in U.S. Pat. Nos. 3,896, 550; 4,209,909; 4,556,387; and 4,721,463, the entirety of which are hereby incorporated by reference. The mounting plates can also be designed for mounting to other full-size articulators, average value articulators, semi-adjustable articulators, fully-adjustable articulators, full-size articulators, handheld articulators, and other types of articulators. Other types of attachment mechanisms can also be employed to mount plates to articulators. Magnets, snaps, adhesives; pins, or other coupling structures can be used to couple the mounting plates to an articulator.

Figure 15:
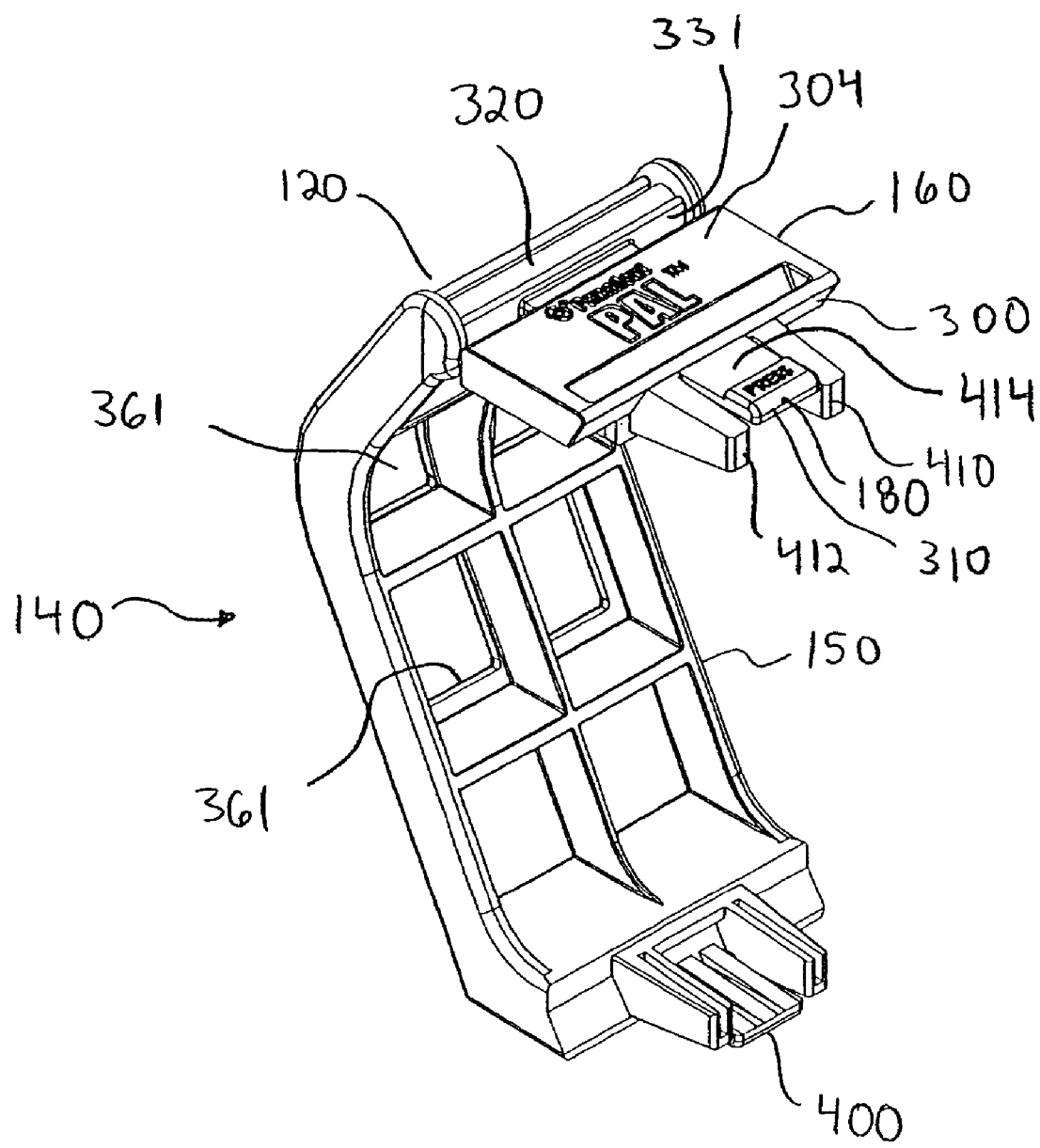
FIG. 15 is a perspective view of an articulator frame that can be coupled to mounting plates.
Figure 16:
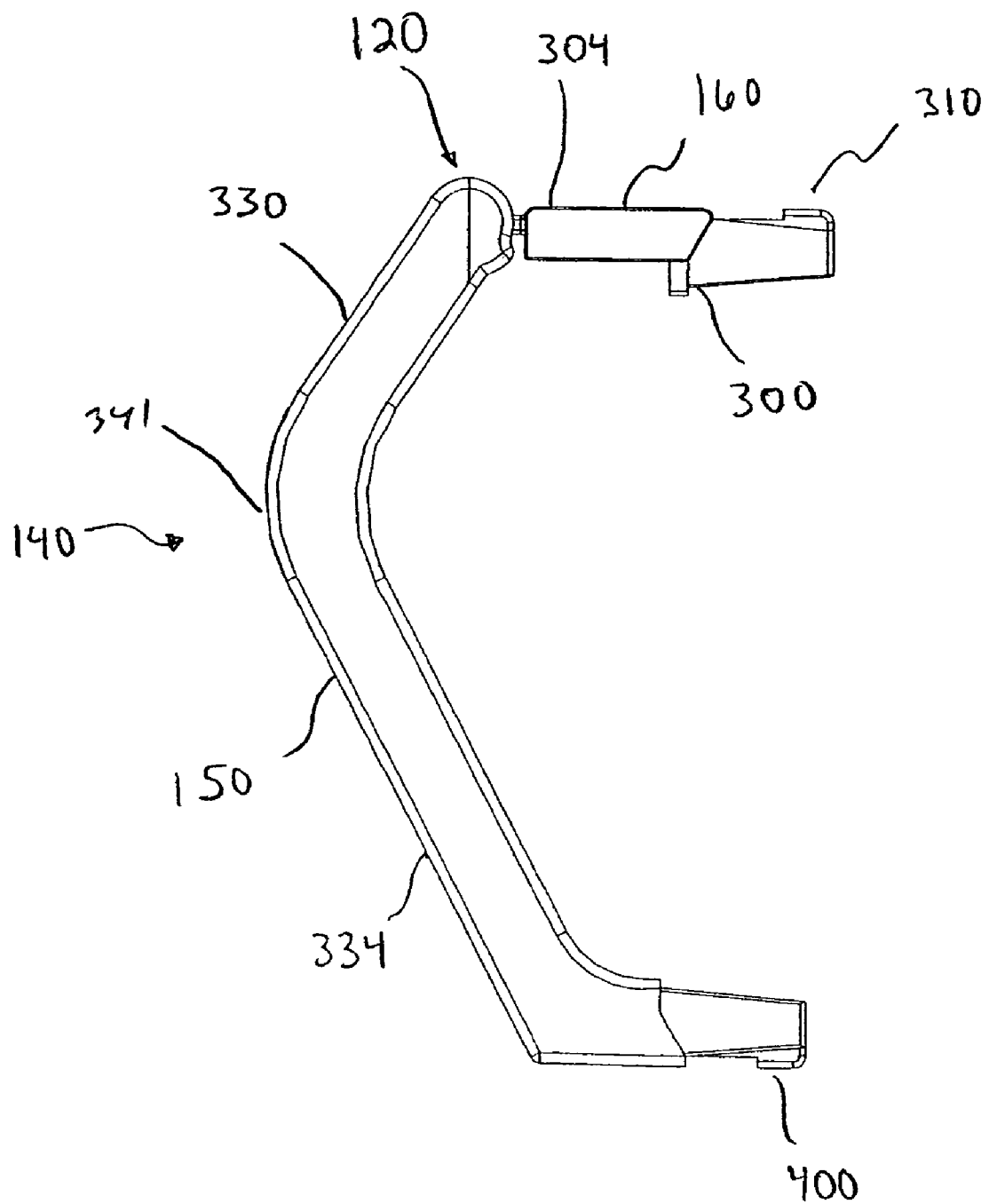
FIG. 16 is side elevational view of the articulator frame of FIG. 15.

FIGS. 15 and 16 illustrate the articulator frame 140 of a handheld articulator having an upper member 160 having a first end 300 for connecting to the upper mounting plate 130. The illustrated first end 300 includes the connector 310 for releasably engaging the upper mounting plate 130. An opposing second end 304 forms a portion of the joint 120.

The joint 120 rotatably connects the upper member 160 and the elongate lower member 150, as discussed above. In some embodiments, including the illustrated embodiment of FIGS. 15 and 16, the joint 120 includes a pin 320 that defines the axis of rotation 122. Each of the members 160, 150 is rotatably mounted to the pin 320. In certain embodiments, the upper member 160 and the lower member 150 are permanently coupled together. Alternatively, the upper member 160 and the elongate lower member 150 are temporarily coupled together. For example, the upper member 160 can snap onto and off of the pin 320. In some embodiments, both the lower member 150 and the upper member 160 can snap onto the pin 320. The member 150 can have a generally U-shaped mount 331 for receiving the pin 320. The pin 320 can be releasably retained in the U-shaped mount 331. As such, the upper member 160 can be separated from the lower member 150, if desired. In one embodiment, rotating the upper frame relative to the lower frame by about 100 degrees will allow separation of the upper and lower members. Various types of joints can be used to couple the second end 304 of the upper member 160 to the elongate lower member 150.

With reference to FIG. 16, the elongate lower member 150 has an upper portion 330 and a lower portion 334, both of which are provided behind the dental casts and in a vertical plane extending through the upper and lower mounting plates 130, 136. These portions 330, 334 form an angle such that the articulator assembly 100 can rest on a support surface 340, as shown in FIG. 6. The configuration of the lower member 150, which may have a substantially flat surface along the lower portion 334, permits the lower portion 334 to rest on the surface 340 while a prosthodontist works with the casts 110, 114.

The illustrated lower member 150 has a curved portion 341 that connects the upper portion 330 to the lower portion 334. The curve of the lower member 150 can be selected to achieve an appropriately built in tilt angle α, as shown in FIG. 6. The angle (is defined between the support surface 340 and a longitudinal axis 360 extending through the central portions of the mounting plates 130, 136. In some non-limiting embodiments, the angle α is about 20°, 30°, 40°, 50°, 60°, and 70°, and ranges encompassing all combinations of such angles. In some preferred non-limiting embodiments, the angle α is in a range of about 50°-70°. As such, the dental casts 110, 114 are positioned so that a user can conveniently and easily view and work on dental prostheses while the articulator assembly 100 remains on the support surface 340. In certain embodiments, the angle α is about 60°. In these embodiments, the user can easily view the dental casts 110, 114 even when the user opens and closes the articulator assembly 100. Of course, the angle α can be chosen based on the position of the surface 340 relative to the user, such as a prosthodontist.

When the articulator assembly 100 rests on the surface 340, the upper dental cast 110 can be moved to an open position while the lower dental cast 114 remains stationary. The articulator assembly 100 can be sufficiently weighed so that the lower portion 334 remains on the surface 340 even when the upper member 160 is rotated to a fully opened position. Accordingly, at least a portion of the articulator frame 140 can remain on a support surface when a user opens and closes the articulator assembly 100.

With reference again to FIGS. 15 and 16, the articulator frame 140 includes the upper connector 310 and a lower connector 400. The connectors 310, 400 can be generally similar to each other, and accordingly, the following description of one of the connectors applies equally to the other, unless indicated otherwise.

The connectors 310, 400 can be releasably coupled to mounting plates 130, 136, respectively. As illustrated, the connectors releasably couple the mounting plates to the articulator frame rearward of the mounting plates. The illustrated upper connector 310 includes the push button 180 interposed between a pair of locators 410, 412. The upper connector 310 is configured so as to fit within the connector port 200 of the upper mounting plate 130 illustrated in FIG. 14.

To attach the mounting plate 130 to the frame 140, the upper connector 310 is inserted through the opening 210 of the mounting plate 130. The connector 310 is then advanced through the connector port 200 until the push button 180 is aligned with the aperture 190. Once the button 180 and aperture 190 are properly aligned, the arm 414 biases the button 180 upwardly until it snaps into place. Once the button 180 extends at least partially through the aperture 190, the plate 130 is coupled to the articulator frame 140.

Figure 17:
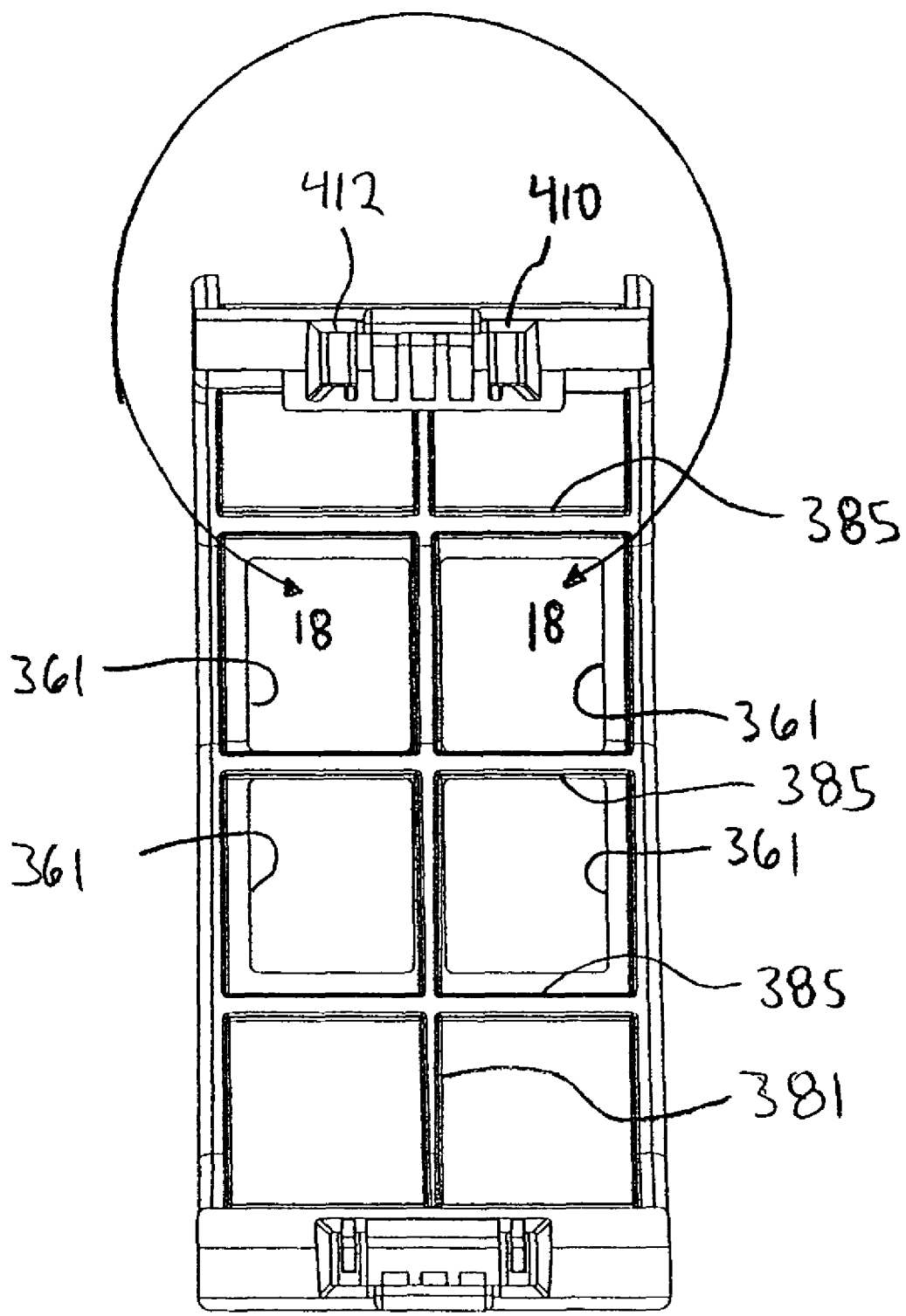
FIG. 17 is a front elevational view of the articulator frame of FIG. 15.
Figure 18:
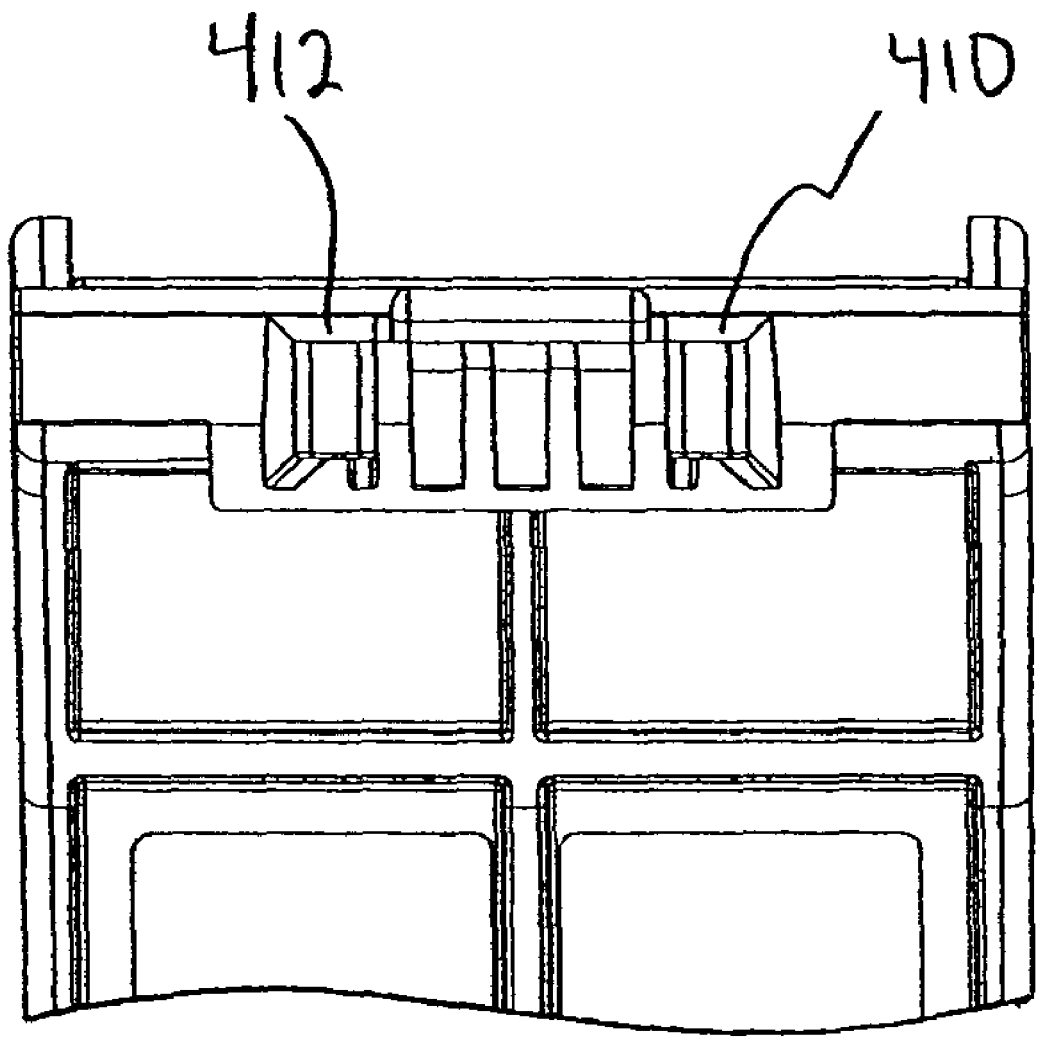
FIG. 18 is an enlarged view of an upper member of the articulator frame of FIG. 17 taken along 18-18.

As shown in FIGS. 16 to 18, the locators 410, 412 are protrusions that extend outwardly from the upper member 160. Locators 410, 412 are preferably configured to be received within slots 214, 216, respectively, of the connector port 200 of FIG. 14. When the connector 310 is disposed within the connector port 200 of the plate 130, the mounting plate 130 is securely held to the upper member 160.

If the upper mounting plate 130 is coupled to the frame 140, as shown in FIG. 7, the push button 180 can be pressed downwardly through the aperture 190. Once the push button 180 is sufficiently depressed, the mounting plate 130 can be pulled away from the upper member 160 thereby sliding the upper connector 310 out of the connector port 200. In this manner, the plate 130 can be removed from the frame 140.

Figure 19:
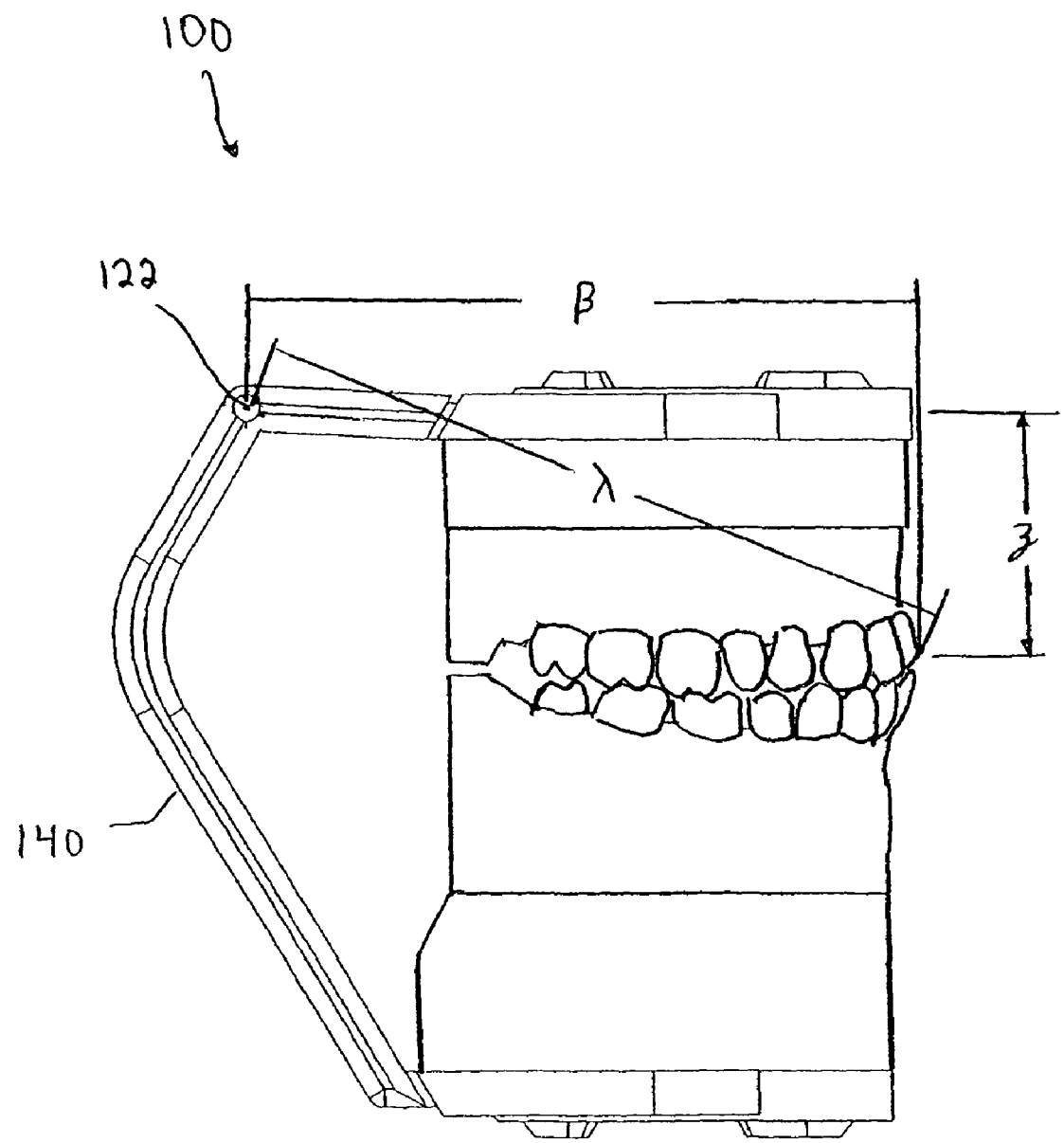
FIG. 19 is a side elevational view of a dental articulator assembly that simulates movement of a human jaw.

With reference to FIG. 19, the axis of rotation 122 can be positioned to provide the desired simulation of a patient's jaw. The articulator frame 140 can be produced in various sizes wherein each size corresponds to a particular sized jaw. For example, some articulator frames can be sized for an average male adult while other frames are sized for an average female adult. The configuration of the articulator frame can be selected based on measurements taken of a patient, patient's age, sex, etc.

In the illustrated embodiment, the distance λ from the axis 122 to the incisal edge is in the range of about 90-110 mm. In preferred embodiments, the distance λ is about 100 mm. Of course, a patient's specific axis-incisal distance λ can vary depending upon the size of the person's mandible or head. The horizontal distance β from the axis 122 to the incisal edge is about 80 mm to about 100 mm. In some embodiments, the distance β is about 85-90 mm. In certain embodiments, the distance β is about 87 mm. The vertical distance ζ between the axis 122 and the incisal edge is about 55-65 mm. In some preferred embodiments, the height ζ is about 60 mm. Of course, these dimensions can be scaled depending upon one or more measurements taken of the patient. That is, the size and configuration of the articulator frame 140 can be selected to correspond generally to the measurements taken from the patient. The dimensions disclosed herein are given by way of example only and are not intended to limit the scope of the disclosure in any way. For example, the dimensions of the articulator frame 140 can be based on Bonwill's equilateral triangle formed by lines from the contact points of the lower central incisors, or the medial line of the residual ridge of the mandible, to the condyle on either side and from one condyle to the other. Additionally or alternatively, the movement of the articulator 100 can be based on Monson's Spherical Theory, which is based on the concept that the mandibular teeth move over the occlusal surfaces of the maxillary teeth and that the radius (or common center) is located in the region of the crista galli. U.S. Pat. No. 6,582,931, incorporated herein by reference, also discloses various techniques for measuring and mounting dental casts. Such articulating assembly 100 provides a substantially accurate anatomically axis of rotation, preferably similar to an axis of rotation of a full-size articulator (e.g., the full-size articulator 10). The axis 122 can generally correspond to the axis of the patient from which the casts 110, 114 were made and related.

In one embodiment, the axis of rotation 122 of the dental articulator is positioned higher than a lower portion of the upper dental cast when the dental articulator is in a closed position. In some embodiments, the axis of rotation is positioned higher than a substantial portion of the upper dental cast when the dental articulator is in a closed position. As illustrated in FIG. 4, in one embodiment when the dental articulator is in a closed position the axis 122 is substantially parallel and horizontal with the upper mounting plate 130.

In one preferred embodiment, the axis of rotation 122 of the articulator assembly 100 substantially corresponds with the hinge axis of the full-size articulator 10 as described above. The axis 122 may be substantially in the same line, or at least at about the same vertical height, as the hinge axis of the full-size articulator, to more closely approximate the hinge axis of a patient. Thus, whether the mounting plates 130, 136 are attached to a handheld articulator such as articulator assembly 100 or to a full-size articulator 10, the mounting plates move relative to each other around about the same axis.

The articulator assembly 100 can also include one or more alignment guides for aligning the upper dental cast 110 and/or the lower dental cast 114. Alignment guides can be used during the fabrication of dental prostheses, diagnosis, testing, and the like. FIGS. 9A and 9B illustrate alignment guides 500, 520 and vertically spaced alignment guides 510, 512, 514. To horizontally align the upper dental cast and the lower dental cast, the alignment guides 520 on the mounting plates 130, 160 can be aligned with the alignment guide 500 extending along the articulator frame 140. Each alignment guide 520 is an indicium on a mounting plate, such as printing, a structural member (e.g., ribs, trusses, protrusions), or any other means, and may be used to verify alignment of prostheses.

The illustrated alignment guide 500 is a linear alignment guide that extends the length of the articulator frame 140. Each of the mounting plates 130, 136 has a vertically extending alignment guide 520 that can be aligned with the vertical alignment guide 500. When the mounting plates 130, 136 are properly aligned, the guides 520, 500 preferably lie generally in the same plane, even as the upper member 160 is articulated. When the dental casts 110, 114 are mounted to the articulator assembly 100, the alignment guides 500, 520 can be used to ensure that the upper member 160 is articulated along the proper path.

With continued reference to FIGS. 9A and 9B, the horizontal alignment guides 510, 512, 514 can be utilized to facilitate proper orientation of the upper and lower dental casts 110, 114. For example, a rod or stick can be clamped between dental casts 110, 114 occupying the closed position, i.e., the stick bite method of alignment. If the rod is not properly aligned with one of the alignment guides 510, 512, 514 the dental casts 110, 114, and/or dental prosthetic can be adjusted to bring the rod into proper alignment.

Any number of alignment aids can be positioned along the lower frame 140. In the illustrated embodiment, the frame 140 has three of horizontal alignment aids 510, 512, 514. In other embodiments, the lower frame 140 has several horizontal alignment aids (e.g., reinforcement ribs) spaced evenly or unevenly vertically along the lower frame 140.

Other alignment guides can also be provided on the articulator assembly 100. Additionally, the alignment guides can be indicia (e.g., printing), structural members (e.g., ribs, trusses, etc.), or any other means for alignment. Various techniques can be used to determine whether there is proper alignment of the dental casts 110, 114. For example, the stick-bite, traditional face-bow, aesthetic ear-bow, the dental facial analyzer, photography, and/or other techniques can be used to ensure proper alignment of the casts 110, 114.

The articulator can have one or more viewing windows. The viewing windows can be positioned along the lower member 150 so that the user can view the upper and lower casts 110, 114 such as from behind. As seen in FIGS. 15 and 17, the lower member 150 has four viewing windows 361. The illustrated viewing windows 361 are generally rectangular; however, the viewing windows can have any shape. The number of viewing windows 361 can be selected to achieve the desired viewing and structural properties of the lower member 150.

One or a plurality of vertical reinforcement ribs 381 can be spaced horizontally and can extend vertically along the lower member 150. A plurality of horizontal reinforcement ribs 385 can be spaced vertically along the lower member 150. The horizontal reinforcement ribs 385 extend horizontally across the lower member 150. The illustrated reinforcement ribs 381, 385 separate the viewing windows 361. The reinforcement ribs 381, 385 can be at other orientations and locations. Any number of reinforcement ribs, gussets, trusses, and/or other structural members can be used to achieve the desired structural properties of the articulator 100. For example, reinforcement ribs can be used to minimize flexure of the articulator 100.

In operation, impressions of a patient's upper teeth are made in impression material positioned on a flat bite fork which is placed and held to the patient's upper teeth. The position of the bite fork in relation to a reference plane on a patient is determined using arbitrary axis face-bow also known as an ear-bow. Other types of techniques such as aesthetic ear-bow or the dental facial analyzer disclosed in U.S. Pat. No. 6,582,931 can be used to determine an appropriate reference planes or axes. The bite fork is then mounted onto a lower frame of the dental articulator in a position to receive the upper dental casts of the patient's teeth. The arbitrary face bow is related to an average distance from the axis of the lower jaw to the ear hole (auditory meatus) and to a third point of reference located somewhere on the patient's face. Other techniques can also be used. Face bows or other instruments can be used to establish proper aesthetic planes of the patient. Various types of aesthetic or functional instruments can be used to record the relation of the maxillae to the hinge axis of rotation of the mandible. As used herein, "aesthetic instruments" is a broad term and includes, but is not limited to, instruments that are used to analyze, measure, or otherwise determine particular dimensions or orientations of a person's or their features. Exemplary aesthetic instruments include, but are not limited to, stick-bites, traditional face-bows, aesthetic ear-bows, the dental facial analyzers, photograph techniques, and combinations thereof.

If a specific axis-incisal distance is to be used, the operator can move the patient's jaw about the temporomandibular joints to locate the approximate hinge axis of the mandible. A physician can measure the distance from this located patient's axis to the patient's maxillary incisal edge and record that distance. This axis-incisal distance can be used to select an appropriately sized articulator assembly 100. In some embodiments, for example, the physician can use the measured distance to select an articulator frame 140 that defines a distance $\lambda$ that is generally similar to the measured axis-incisal distance.

Molds can be used to make the dental casts. The molds preferably have impressions of a person's teeth. These molds are then used to make casts that correspond to the shape and size of the person's teeth. Various materials can be used to form the dental casts. Non-limiting exemplary materials include, but are not limited to, plaster, polymers, plastics, stone, or other materials having suitable physical properties. The casts can then be mounted to an articulator to define proper functional and/or aesthetic relationships between the casts.

An articulator (e.g., the articulator 10 or other full-size articulator) can be used to mount the dental casts to the mounting plates 130, 136. While a cast is held in proper position, it is secured by dental plaster to a mounting plate, such as the mounting plate 130 attached to the upper frame of a dental articulator. An index tray can be used to position the upper cast. In some embodiments, mounting material, such as plaster, can be placed on the mounting plate 130 and the upper cast 110 such that the mounting plate 130 can be coupled to the upper cast 110.

Once the upper cast is mounted, the lower cast can be secured to the articulator by utilizing the upper dental cast as a guide along with an interocclusal record. The interocclusal record can record the spatial relationship of the person's jaw, including, but not limited to, the intercuspal position, maximum intercuspation position, completely occluded position of the upper and lower teeth, centric relation when the position of the mandible when the condyles are in an orthopedically stable position, or other recorded position. The dental casts are preferably positioned in the same relation to each other as the teeth in the patient's mouth and face for esthetic evaluation or study, as well as being properly oriented to the patient's hinge axis for functional evaluation or study.

In alternative embodiments, the dental casts 110, 114 can be mounted to the mounting plates 130, 136 without utilizing an articulator. For example, the dental casts 110, 114 can be manually mounted to the mounting plates 130, 136 without the aid of an articulator, such as the full-size articulator 10. A technician can visually align and mount the dental casts 110, 114. Other types of mounting methods can also be employed. However, these types of mounting methods typically do not align the casts 110, 114 with the same level of accuracy when using a dental articulator with a face bow or other facial analyzer, such as the dental facial analyzer disclosed in U.S. Pat. No. 6,582,931.

After the upper and lower dental casts 110, 114 are mounted to corresponding mounting plates 130, 136 on the articulator 10, the mounting plates 130, 136 and corresponding dental casts 110, 114 can be coupled to the portable articulator frame 140. In the illustrated embodiment, the upper mounting plate 130 can be coupled to the upper connector 310 and the lower mounting plate 136 can be coupled to the lower connector 400. After the mounting plates 130, 136 are attached to the articulator frame 140, as shown in FIGS. 4 and 5, a user can use the articulator assembly 100. During the prostheses fabrication process, the user can articulate the articulator assembly 100 about the axis 122 as indicated by the arrow 131. The articulator assembly 100 can be opened and closed repeatedly to help the user simulate movement of a patient's jaw and ensure proper sizing, fit, and placement of any prosthesis. Because the articulator assembly 100 has a generally anatomically correct axis of rotation to match the jaw rotation of the patient, a dental prosthesis fabricated utilizing the articulator assembly 100 should properly fit within the patient's mouth. Various known fabrication techniques can be performed while the dental casts 110, 114 are mounted to the articulator assembly 100.

In some embodiments, the handheld dental articulator 100 is the only articulator used to make a dental prosthesis. In alternative embodiments, the handheld dental articulator 100 is used in conjunction with a full-size dental articulator to either mount the casts to the mounting plates or to fabricate one or more dental prostheses. In some variations, the handheld dental articulator 100 is used to fabricate most of the prosthesis. To make the final adjustments to the prosthesis, the prosthesis on the casts 110, 114 connected to mounting plates 130, 136 can be mounted or put back on (attached) to the full-size articulator and then worked upon by the prosthodontists.

In some embodiments, after the dental articulator 100 is used, the mounting plates 130, 136 are mounted or put back on (attached) to a full-size articulator to perform tests or additional fabrication processes. The mounting plates 130, 136 and associated casts 110, 114 can be moved between the handheld articulators 100 and full-size articulators as many times as needed, or desired.

The same dental casts 110, 114 can be mounted or attached to handheld articulators and full-size articulators that have generally similar axes of rotations. As such, a similar path of travel can be provided for the casts even though a handheld articulator assembly has a relatively simple design. This provides consistency between the articulators to reduce fabrication time, improve tolerancing of prostheses, and the like.

Various materials can be used to construct the articulator assembly 100. Metals, plastics, polymers, and other structural materials can be used to form any of the components of the articulator assembly 100. The articulator frame 140 can be constructed of metal (e.g., aluminum, steel including stainless steel, or other alloys) for a substantially rigid frame. These articulator frames may be multi-use frames. In alternative embodiments, the articulator frame 140 can comprises a polymer, preferably a structural polymer. Suitable rigid but flexible materials include, for example, but without limitation: plastics or composites (e.g., carbon fiber composites), polypropylene, polyethylene, polycarbonate, polyvinylchloride, acrylonitrile butadiene styrene, nylon, olefin, acrylic, polyester, thermoplastic urethane, thermoplastic elastomers, thermoset plastics and the like. Other materials can also be employed. In some non-limiting embodiments, the articulator frame 140 is comprised of acrylonitrile butadiene styrene. The articulator frame 140 can be a relatively lightweight structure. In some embodiments, the articulator frame 140 weighs substantially less than a full-size dental articulator. The dental casts can be moved between a full-size articulator and the handheld articulator that weighs less than 90%, 80%, 70%, 50%, 30%, and 20% of the full-size articulator. The frame 140 can have reinforcing members or structures to increase its stiffness. For example, the frame 140 can have one or more reinforcing ribs for increasing the stiffness of the frame 140, as desired.

All patents and publications mentioned herein are hereby incorporated by reference in their entireties. Except as further described herein, the embodiments, features, systems, devices, materials, methods and techniques described herein may, in some embodiments, be similar to any one or more of the embodiments, features, systems, devices, materials, methods and techniques described in U.S. Pat. Nos. 3,593,424, 3,694,919, 3,896,550, 4,034,475, 4,209,909, 4,352,662, 4,543,062, 4,556,387, 4,600,385, 4,693,683, 4,721,463, 6,109,917, 6,582,931. In addition, the embodiments, features, systems, devices, materials, methods and techniques described herein may, in certain embodiments, be applied to or used in connection with any one or more of the embodiments, features, systems, devices, materials, methods and techniques disclosed in the above-mentioned U.S. Pat. Nos. 3,593,424, 3,694,919, 3,896,550, 4,034,475, 4,209,909, 4,352,662, 4,543,062, 4,556,387, 4,600,385, 4,693,683, 4,721,463, 6,109,917, 6,582,931. The above-mentioned U.S. Pat. Nos. 3,593,424, 3,694,919, 3,896,550, 4,034,475, 4,209,909, 4,352,662, 4,543,062, 4,556,387, 4,600,385, 4,693,683, 4,721,463, 6,109,917, 6,582,931 are hereby incorporated by reference herein and made a part of this specification.

The articles disclosed herein may be formed through any suitable means. For example, the articles can be formed through injection casting, extrusion (including co-extrusion), and compression casting. For example, the frame 140 can be formed through an injection casting process. The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

The handheld articulator 100 is primarily described in conjunction with a full-size articulator. However, the handheld articulator 100 can be used with one or more of the following: average value articulators, semi-adjustable articulators, fully-adjustable articulators, full-size articulators, handheld articulators, and other types of articulators. As such, mounting plates can be compatible with these various types of articulators (either arcon or non-arcon articulators). Mounting plates can be temporarily or permanently mounted to these articulators. Additionally, the handheld articulator 100 can be used alone, i.e., without using any other articulator. In some embodiments, the handheld articulator 100 is an average value articulator. Advantageously, the handheld articulator 100 can have a simple design and can be used simulate the positions and movements of typical people. The handheld 100 may or may not have some angle or side shift built-in.

Furthermore, the skilled artisan will recognize the interchangeability or compatibility of various features from different embodiments disclosed herein. Similarly, the various features and steps discussed above, as well as other known equivalents for each such feature or step, can be mixed and matched by one of ordinary skill in this art to perform methods in accordance with principles described herein. Additionally, the methods which are described and illustrated herein are not limited to the exact sequence of acts described, nor are they necessarily limited to the practice of all of the acts set forth. Other sequences of events or acts, or less than all of the events, or simultaneous occurrence of the events, may be utilized in practicing the embodiments of the invention.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein.

What is claimed is:

1. A handheld dental articulator, comprising:
   a handheld articulator frame comprising an upper member and a lower member, wherein the handheld articulator frame has a pivot axis connecting the upper member to the lower member;
   an upper mounting plate configured to hold an upper dental cast connected to the upper member; and
   a lower mounting plate configured to hold a lower dental cast connected to the lower member;
   wherein the pivot axis of the handheld articulator is located at a natural hinge axis of rotation of a patient when the upper and lower dental casts are respectively held by the upper and lower mounting plates;
   wherein the upper mounting plate has an upper surface, a lower surface, a front end, and a rear end, the upper mounting plate having a first attachment mechanism at the rear end of the upper mounting plate configured to removably connect to the upper member of the handheld articulator frame rearwardly of the upper mounting plate, and a second attachment mechanism at the upper surface of the upper mounting plate configured to removably connect the upper surface of the upper mounting plate to an upper member of a full-size articulator frame;
   wherein the lower mounting plate has an upper surface, a lower surface, a front end, and a rear end, the lower mounting plate having a first attachment mechanism at the rear end of the lower mounting plate configured to removably connect to the lower member of the handheld articulator frame rearwardly of the lower mounting plate, and a second attachment mechanism at the lower surface of the lower mounting plate configured to removably connect the lower surface of the lower mounting plate to a lower member of the full-size articulator frame; and
   wherein articulation of the upper and lower mounting plates about the pivot axis of the handheld articulator frame with the dental casts respectively held by the upper and lower mounting plates and with the upper and lower mounting plates connected to the handheld articulator frame simulates actual jaw movements of the patient about an anatomically correct hinge axis of rotation.

2. The dental articulator of claim 1, wherein the pivot axis is positioned higher than a substantial portion of the upper dental cast.

3. The dental articulator of claim 1, wherein the pivot axis is substantially parallel and horizontal with the upper mounting plate.

4. The dental articulator of claim 1, wherein the handheld articulator frame extends behind a location of the upper and lower dental casts in a vertical plane extending through the upper and lower mounting plates.

5. The dental articulator of claim 4, wherein the lower member of the handheld articulator frame extends rearwardly and upwardly behind the dental casts.

6. The dental articulator of claim 1, wherein the upper and lower mounting plates have at least one indicium for a vertical reference guide.

7. The dental articulator of claim 1, wherein the handheld articulator frame comprises at least one vertical alignment guide.

8. The dental articulator of claim 1, wherein the upper and lower members have plate-like portions with substantially rectangular cross-sections.

9. The dental articulator of claim 1, wherein the handheld articulator frame comprises at least one horizontal alignment guide.

10. The dental articulator of claim 1, wherein the handheld articulator frame is made of plastic.

11. The dental articulator of claim 1, wherein the lower member is V-shaped.

12. The dental articulator of claim 1, wherein the lower member has an upper portion and a lower portion, the lower portion having a substantially flat surface adapted to permit the lower portion to rest on a surface, the upper portion being formed at an angle to the lower portion configured to position the dental casts at a desired viewing angle while the lower portion rests on the support surface.

13. The dental articulator of claim 1, wherein the upper and lower members of the handheld articulator frame each has a width that is no wider than a width of either of the upper and lower mounting plates.

14. The dental articulator of claim 1, wherein a height of the handheld articulator frame is not substantially greater than a vertical distance between the upper and lower mounting plates.

15. A dental articulator system, comprising:
    a handheld articulator frame comprising an upper member and a lower member, wherein the handheld articulator frame is configured to pivot the upper and lower members about a pivot axis;
    an upper mounting plate configured to hold an upper dental cast of a patient removably connectable to the upper member; and
    a lower mounting plate configured to hold a lower dental cast of the patient removably connectable to the lower member;
    wherein the pivot axis of the handheld articulator frame is located at a natural hinge axis of rotation of the patient when the upper and lower dental casts are respectively held by the upper and lower mounting plates and the upper and lower mounting plates are respectively connected to the upper and lower members of the handheld articulator frame;
    the upper mounting plate having an upper surface, a lower surface, a front end and a rear end, the upper mounting plate having a first attachment mechanism at the rear end of the upper mounting plate configured to removably connect the rear end of the upper mounting plate to the upper member of the handheld articulator frame rearwardly of the upper mounting plate, and a second attachment mechanism at the upper surface of the upper mounting plate configured to removably connect the upper surface of the upper mounting plate to an upper member of a full-size articulator frame;

the lower mounting plate having an upper surface, a lower surface, a front end and a rear end, the lower mounting plate having a first attachment mechanism at the rear end of the lower mounting plate configured to removably connect the rear end of the lower mounting plate to the lower member of the handheld articulator frame rearwardly of the lower mounting plate, and a second attachment mechanism configured to removably connect the lower surface of the lower mounting plate to a lower member of a full-size articulator frame; and wherein articulation of the upper and lower mounting plates about the pivot axis of the handheld articulator frame with the upper and lower dental casts respectively held by the upper and lower mounting plates and with the upper and lower mounting plates respectively connected to the upper and lower members of the handheld articulator frame simulates actual jaw movements of the patient about an anatomically correct hinge axis of rotation.

16. The dental articulator system of claim 15, wherein the upper and lower members of the handheld articulator frame are removably coupled to the upper and lower mounting plates, respectively.

17. The dental articulator system of claim 15, further comprising a full-size articulator frame comprising:

an upper member and a lower member, wherein the full-size articulator frame is configured to pivot the upper and lower members of the full-size articulator frame about a pivot axis, wherein the pivot axis of the full-size articulator frame is located at a natural hinge axis of rotation of the patient when the upper and lower dental casts are respectively held by the upper and lower mounting plates and the upper and lower mounting plates are respectively connected to the upper and lower members of the full-size articulator frame;

wherein articulation of the upper and lower mounting plates about the pivot axis of the full-size articulator frame with the upper and lower dental casts respectively held by the upper and lower mounting plates and with the upper and lower mounting plates respectively connected to the upper and lower members of the full-size articulator frame simulates actual jaw movements of the patient about an anatomically correct hinge axis of rotation;

wherein the pivot axis of the handheld articulator is the same as the pivot axis of the full-size articulator when the upper and lower mounting plates respectively holding the upper and lower dental casts are connected to either the handheld articulator frame or the full-size articulator frame.

18. The dental articulator system of claim 15, wherein the first attachment mechanism of the upper and lower mounting plates comprises a snap fitting.

19. The dental articulator system of claim 15, wherein the second attachment mechanism of the upper and lower mounting plates comprises a magnetic connection.

20. The dental articulator system of claim 15, further comprising an upper dental cast connected to the upper mounting plate and a lower dental cast connected to the lower mounting plate.

21. The dental articulator of claim 15, wherein the upper mounting plate comprises a single piece of material that includes both the first and second attachment mechanisms and the lower mounting plate comprises a single piece of material that includes both the first and second attachment mechanisms.

22. The dental articulator system of claim 15, wherein the upper mounting plate comprises a single piece of material that includes both the first and second attachment mechanisms and the lower mounting plate comprises a single piece of material that includes both the first and second attachment mechanisms.

23. A dental articulator system, comprising:

a handheld articulator comprising a handheld articulator frame having upper and lower members, the handheld articulator having a pivot axis to pivot the upper member relative to the lower member;

an upper mounting plate removably connectable with the upper member of the handheld articulator frame configured to hold an upper dental cast of a patient;

a lower mounting plate removably connectable with the lower member of the handheld articulator frame configured to hold a lower dental cast of the patient;

wherein the pivot axis of the handheld articulator simulates actual jaw movements of the patient about an anatomically correct hinge axis of rotation when the upper and lower dental casts are respectively held by the upper and lower mounting plates and the upper and lower mounting plates are respectively connected with the upper and lower members of the handheld articulator frame;

a full-size articulator having an upper frame and a lower frame, the full-size articulator having a pivot axis to pivot the upper frame relative to the lower frame;

wherein the upper and lower mounting plates are removably connectable to the upper and lower frames of the full-size articulator to allow rotation of the upper and lower mounting plates about the pivot axis of the full-size articulator, wherein the pivot axis of the full-size articulator simulates actual jaw movements of the patient about an anatomically correct hinge axis of rotation when the upper and lower dental casts are respectively held by the upper and lower mounting plates and the upper and lower mounting plates are respectively connected with the upper and lower frames of the full-size articulator; and wherein when the upper and lower mounting plates are connected to either the handheld articulator or the full-size articulator, the pivot axis of the handheld articulator is the same as the pivot axis of the full-size articulator.

24. A method of simulating human jaw movement, the method comprising:

providing an upper mounting plate coupled to an upper dental cast and a lower mounting plate coupled to a lower dental cast;

removably coupling the upper and lower mounting plates to a first dental articulator, the first dental articulator being configured to pivot the upper mounting plate relative to the lower mounting plate on a first axis of rotation that simulates actual jaw movements about an anatomically correct hinge axis of a patient;

removing the upper and lower mounting plates from the first dental articulator; and removably coupling the upper and lower mounting plates to a second dental articulator, the second dental articulator being configured to pivot the upper mounting plate relative to the lower mounting plate on a second axis of rotation that simulates actual jaw movements of the patient about an anatomically correct hinge axis of rotation, wherein the second axis is the same as the first axis, and wherein one of the first and second articulators is a full-size articulator and the other of the first and second articulators is a handheld articulator smaller than the full size articulator.

25. The method of claim 24, wherein the first dental articulator is a full-size articulator and the second dental articulator is a handheld articulator.

26. The method of claim 25, further comprising removing the upper and lower mounting plates from the second articulator and re-coupling the upper and lower mounting plates to the first articulator.

27. The method of claim 24, wherein the first dental articulator is a handheld articulator and the second dental articulator is a full-size articulator.

28. The method of claim 24, wherein the handheld articulator comprises an articulator frame having a pivot axis above a lower portion of the upper dental cast.

29. The method of claim 24, wherein the upper and lower mounting plates are removably coupled to the handheld articulator by a snap fitting.

30. The method of claim 29, wherein the upper and lower mounting plates are removably coupled to the full-size articulator by magnets.

31. The method of claim 24, wherein the handheld articulator weighs less than 20% of a weight of the full-size articulator.

* * * * *

UNITED STATES PATENT AND TRADEMARK OFFICE
CERTIFICATE OF CORRECTION

| | | |
|---|---|---|
| PATENT NO. | : 7,857,622 B2 | Page 1 of 1 |
| APPLICATION NO. | : 11/542349 | |
| DATED | : December 28, 2010 | |
| INVENTOR(S) | : Thomas E. Lee | |

It is certified that error appears in the above-identified patent and that said Letters Patent is hereby corrected as shown below:

At Page 1 (Item 75), Line 1, please delete "Tomas" and insert therefore, -- Thomas --.

At Page 2 (Item 56), Column 1, Line 3, under Other Publications, please delete "Denistry" and insert therefore, -- Dentistry --.

At Column 14, Line 66, please delete "(is" and insert therefore, -- $\alpha$ is --.

At Column 16, Line 4, please delete "$\lambda$from" and insert therefore, -- $\lambda$ from --.

At Column 16, Line 7, please delete "$\lambda$can" and insert therefore, -- $\lambda$ can --.

At Column 24, Line 5, In Claim 21, after "articulator" please insert -- system --.

Signed and Sealed this
Fourteenth Day of August, 2012

David J. Kappos
*Director of the United States Patent and Trademark Office*